US007846667B2

(12) United States Patent
Jen et al.

(10) Patent No.: US 7,846,667 B2
(45) Date of Patent: Dec. 7, 2010

(54) METHODS FOR THE DIAGNOSIS AND TREATMENT OF LUNG CANCER

(75) Inventors: Jin Jen, Baltimore, MD (US); Gary A. Beaudry, Montclair, NJ (US); Stephen L. Madden, Sudbury, MA (US); Arthur H. Bertlesen, Ridgewood, NJ (US); David Sidransky, Baltimore, MD (US)

(73) Assignees: Genzyme Corporation, Framingham, MA (US); Johns Hopkins University, Baltimore, MD (US)

( * ) Notice: Subject to any disclaimer, the term of this patent is extended or adjusted under 35 U.S.C. 154(b) by 0 days.

(21) Appl. No.: 12/545,028

(22) Filed: Aug. 20, 2009

(65) Prior Publication Data

US 2010/0062443 A1 Mar. 11, 2010

Related U.S. Application Data

(60) Division of application No. 11/504,260, filed on Aug. 14, 2006, now abandoned, which is a continuation of application No. 09/646,478, filed as application No. PCT/US99/06947 on Mar. 30, 1999, now abandoned.

(60) Provisional application No. 60/080,044, filed on Mar. 31, 1998.

(51) Int. Cl.
*C12Q 1/68* (2006.01)
(52) U.S. Cl. ............................ 435/6; 435/7.1; 536/23.5; 536/24.31; 536/24.33; 530/350; 530/387.1; 530/387.7; 436/64
(58) Field of Classification Search .................... 435/6, 435/7.1; 536/23.5, 24.31, 24.33; 530/350, 530/387.1, 387.7; 436/64
See application file for complete search history.

(56) References Cited

U.S. PATENT DOCUMENTS

| 3,817,837 | A | 6/1974 | Rubenstein et al. |
| 3,850,752 | A | 11/1974 | Schuurs et al. |
| 3,939,350 | A | 2/1976 | Kronick et al. |
| 3,996,345 | A | 12/1976 | Ullman et al. |
| 4,275,149 | A | 6/1981 | Litman et al. |
| 4,277,437 | A | 7/1981 | Maggio |
| 4,366,241 | A | 12/1982 | Tom et al. |
| 4,603,102 | A | 7/1986 | Himmelmann et al. |
| 5,405,783 | A | 4/1995 | Pirrung et al. |
| 5,412,087 | A | 5/1995 | McGall et al. |
| 5,445,934 | A | 8/1995 | Fodor et al. |
| 5,464,764 | A | 11/1995 | Capecchi et al. |
| 5,487,992 | A | 1/1996 | Capecchi et al. |
| 5,578,444 | A | 11/1996 | Edwards et al. |
| 5,578,832 | A | 11/1996 | Trulson et al. |
| 5,627,059 | A | 5/1997 | Capecchi et al. |
| 5,631,153 | A | 5/1997 | Capecchi et al. |
| 5,631,734 | A | 5/1997 | Stern et al. |
| 5,695,937 | A | 12/1997 | Kinzler et al. |
| 5,695,980 | A | 12/1997 | Wei et al. |
| 5,734,039 | A | 3/1998 | Calabretta et al. |
| 5,888,796 | A | 3/1999 | Chang |
| 2004/0166527 | A1* | 8/2004 | Beaudry et al. ............ 435/6 |
| 2007/0054274 | A1* | 3/2007 | Giordano .................. 435/6 |

FOREIGN PATENT DOCUMENTS

| CA | 2178022 | 12/1996 |
| EP | 0717 113 A2 | 6/1996 |
| JP | H2-53486 | 2/1990 |
| WO | WO 94/07538 A1 | 4/1994 |
| WO | WO 95/20681 | 8/1995 |
| WO | WO 97/10365 | 3/1997 |
| WO | WO 99/50278 | 10/1999 |

OTHER PUBLICATIONS

Amatschek et al. (Cancer Res. Feb. 1, 2004; 64: 844-856).*
Lyon et al. (Crit. Rev. Oncog. 1994; 5 (4): 373-388).*
Borges et al. (1997) "An *achaete-scute* homologue essential for neuroendocrine differentiation in the lung," *Nature* 386:852-855.
Chen et al. (1994) "The second intron of the K-*ras* gene contains regulatory elements associated with mouse lung tumor susceptibility," *Proc. Natl. Acad. Sci. USA* 91:1589-1593.
Chiang et al. (1991) "Antisense oligonucleotides inhibit intercellular adhesion molecule 1 expression by two distinct mechanisms," *J. Biol. Chem.* 266:18162-18171.
Chisaka et al. (1992) "Developmental defects of the ear, cranial nerves and hindbrain resulting from targeted disruption of the mouse homeobox Gene *Hox-1.6*," *Nature* 355:516-520.
Day & Thompson (1987) "Molecular cloning of cDNA coding for human PGP 9.5 protein," *FEBS Letters* 210(2):157-160.
Dhillon et al. (1985) "Neural markers in carcinoma of the lung," *Br. J. Cancer* 51:645-652.
Dorin et al. (1992) "Cystic fibrosis in the mouse by targeted insertional mutagenesis," *Nature* 359:211-215.
Ermisch et al. (1995) "Protein gene product (PGP) 9.5 in diagnostic (neuro-) oncology. An immunomorphological study," *Clin. Neuropath.* 14(3):130-136.
Gadzar et al. (1996) "NCI Series of Cell Lines: A Historical Perspective," *J. Cell Biochem. Suppl.* 24:1-11.
Gilbert et al. (1997) "Low specificity of PGP9.5 expression for detection of micrometastatic neuroblastoma," *Brit. J. Cancer* 75(12):1779-1781.
Golay et al. (1991) "Expression of C-myb and B-myb, but not A-myb, correlates with the proliferation in human hematopoietic cells," *Blood* 77(1):149-158.
Golay et al. (1996) "Expression of A-myb, but not c-myb and B-myb, is Restricted to Burkitt's Lymphoma, slg+ B-Acute Lymphoblastic Leukemia, and a Subset of Chronic Lymphocytic Leukemias," *Blood* 87(5):1900-1911.
Golay et al. (1997) "Redundant Functions of B-Myb and c-Myb in Differentiating Myeloid Cells," *Cell Growth & Differentiation* 8:1305-1316.

(Continued)

*Primary Examiner*—Stephen L Rawlings
(74) *Attorney, Agent, or Firm*—Antoinette F. Konski; Foley & Lardner LLP

(57) ABSTRACT

The present invention provides methods for aiding in the diagnoses of the neoplastic condition of a lung cell and methods of screening for a potential therapeutic agent for the reversal of the neoplastic condition.

13 Claims, 3 Drawing Sheets

OTHER PUBLICATIONS

Gupta et al. (1995) "Regulation of an eukaryotic initiation factor-2 (eIF-2) associated with 67 kDa Glycoprotein (p67) and its requirement in protein synthesis," *Gene Expression* 5(2):113-122.

Hibi et al. (1991) "Serial Analysis of Gene Expression in Non-Small cell Lung Cancer," *Cancer Research* 58:5690-5694.

Hibi et al. (1999) "Frequent overexpression of PGP9.5 in a non-small cell lung cancer," *Proceedings of the American Association of Cancer Research* 40:610.

Hojo et al. (1998) "Overexpression of p53 protein in interstitial lung disease," *Respiratory Medicine* 92:184-190.

Kasai et al. (1992) "Pulmonary Large Cell Carcinoma Expressing Neuroendocrine Markers: the Morphological, Biological, and Neuroendocrine Features of Their Cell Lines and Surgical Cases," *Jpn. J. Cancer Res.* 83:1002-1010.

Kroegel et al. (1996) "Expression von Proto-Onkogenen, Tumor-Suppressor-Genen und dominanten Onkogenen bei Malignomen der Lunge," *Atemw.-Lungenkrkh* 2:133-142.

Madden et al. (1997) "SAGE transcript profiles for p53-dependent growth regulation," *Oncogene* 15:1079-1085.

Mooi et al. (1988) "Non-small cell lung carcinomas with neuroendocrine features. A light microscopic, immunohistochemical and ultrastructural study of 11 cases," *Histopathology* 13:329-337.

Nomura et al. (1988) "Isolation of human cDNA clones of *myb*-related genes, A-*myb* and B-*myb*," *Nucleic Acids Research* 16(23):11075-11089.

Phelps et al. (1996) "NCI-Navy medical oncology branch cell line data base," *J. Cell Biochem. Suppl.* 24:32-91.

Rosenwald (1996) "Upregulated expression of the genes coding translation initiation factors eIF-4E and eIF-2α in transformed cells," *Cancer Letters* 102:113-123.

Salgia et al. (1998) "Molecular Abnormalities in Lung Cancer," *J. of Clinical Oncology* 16(3):1207-1217.

Satterwhite et al. (1994) "Inhibition of Cell Growth by TGFβ1 is Associated with Inhibition of B-*myb* and *Cyclin A* in both BALB/MK and Mv1Lu Cells," *Cell Growth & Differentiation* 5:789-799.

Stein (1999) "Keeping the biotechnology of antisense in context," *Nature Biotech.* 17(3):209.

Velculescu et al. (1995) "Serial analysis of gene expression," *Science* 270:484-487.

Venter et al. (1996) "A new strategy for genome sequencing," *Nature* 381:364-366.

Wani et al. (1998) "Enhanced expression of the 8*oxo*-7,8-*dihydrodeoxyguanosine triphosphatase* gene in human breast tumor cells," *Cancer Letters* 125:123-130.

Wilkinson et al. (1989) "The neuron-specific protein PGP 9.5 is a ubiquitin carboxyl-terminal hydrolase," *Science* 246:670-673.

Wu & Wu (1987) "Receptor-mediated in vitro gene transformation by a soluble DNA carrier system," *J. Biol. Chem.* 262:4429-4432.

\* cited by examiner

```
                       SEQUENCE LISTING

<160> NUMBER OF SEQ ID NOS: 17

<210> SEQ ID NO 1
<211> LENGTH: 10
<212> TYPE: DNA
<213> ORGANISM: Artificial
<220> FEATURE:
<223> OTHER INFORMATION: Probe for b-myb

<400> SEQUENCE: 1
tgctgccctg                                                             10

<210> SEQ ID NO 2
<211> LENGTH: 10
<212> TYPE: DNA
<213> ORGANISM: Artificial
<220> FEATURE:
<223> OTHER INFORMATION: probe for PGP9.5

<400> SEQUENCE: 2
cagtctaaaa                                                             10

<210> SEQ ID NO 3
<211> LENGTH: 10
<212> TYPE: DNA
<213> ORGANISM: Artificial
<220> FEATURE:
<223> OTHER INFORMATION: Probe for 8-oxo-dGTPase

<400> SEQUENCE: 3
tggcccgacg                                                             10

<210> SEQ ID NO 4
<211> LENGTH: 10
<212> TYPE: DNA
<213> ORGANISM: Artificial
<220> FEATURE:
<223> OTHER INFORMATION: Probe for p67

<400> SEQUENCE: 4
taatactttt                                                             10
```

```
<210> SEQ ID NO 5
<211> LENGTH: 10
<212> TYPE: DNA
<213> ORGANISM: Artificial
<220> FEATURE:
<223> OTHER INFORMATION: SAGE tag

<400> SEQUENCE: 5
tgtacctgta                                                                10

<210> SEQ ID NO 6
<211> LENGTH: 10
<212> TYPE: DNA
<213> ORGANISM: Artificial
<220> FEATURE:
<223> OTHER INFORMATION: SAGE tag

<400> SEQUENCE: 6
gcttgaataa                                                                10

<210> SEQ ID NO 7
<211> LENGTH: 10
<212> TYPE: DNA
<213> ORGANISM: Artificial
<220> FEATURE:
<223> OTHER INFORMATION: SAGE Tag

<400> SEQUENCE: 7
atgcagccat                                                                10

<210> SEQ ID NO 8
<211> LENGTH: 10
<212> TYPE: DNA
<213> ORGANISM: Artificial
<220> FEATURE:
<223> OTHER INFORMATION: SAGE Tag

<400> SEQUENCE: 8
ctcctgggcg                                                                10

<210> SEQ ID NO 9
<211> LENGTH: 10
<212> TYPE: DNA
<213> ORGANISM: Artificial
<220> FEATURE:
<223> OTHER INFORMATION: SAGE Tag

<400> SEQUENCE: 9
ccaggggaga                                                                10

<210> SEQ ID NO 10
<211> LENGTH: 10
<212> TYPE: DNA
<213> ORGANISM: Artificial
<220> FEATURE:
<223> OTHER INFORMATION: SAGE Tag

<400> SEQUENCE: 10
ctgagacgaa                                                                10

<210> SEQ ID NO 11
<211> LENGTH: 10
<212> TYPE: DNA
<213> ORGANISM: Artificial
<220> FEATURE:
<223> OTHER INFORMATION: SAGE Tag
```

```
<400> SEQUENCE: 11
gatagcacag                                                          10

<210> SEQ ID NO 12
<211> LENGTH: 10
<212> TYPE: DNA
<213> ORGANISM: Artificial
<220> FEATURE:
<223> OTHER INFORMATION: SAGE Tag

<400> SEQUENCE: 12
tatctgtcta                                                          10

<210> SEQ ID NO 13
<211> LENGTH: 10
<212> TYPE: DNA
<213> ORGANISM: Artificial
<220> FEATURE:
<223> OTHER INFORMATION: SAGE Tag

<400> SEQUENCE: 13
taatactttt                                                          10

<210> SEQ ID NO 14
<211> LENGTH: 10
<212> TYPE: DNA
<213> ORGANISM: Artificial
<220> FEATURE:
<223> OTHER INFORMATION: SAGE Tag

<400> SEQUENCE: 14
caataaaatt                                                          10

<210> SEQ ID NO 15
<211> LENGTH: 10
<212> TYPE: DNA
<213> ORGANISM: Artificial
<220> FEATURE:
<223> OTHER INFORMATION: SAGE Tag

<400> SEQUENCE: 15
aaggctggaa                                                          10

<210> SEQ ID NO 16
<211> LENGTH: 10
<212> TYPE: DNA
<213> ORGANISM: Artificial
<220> FEATURE:
<223> OTHER INFORMATION: SAGE Tag

<400> SEQUENCE: 16
ttctgtgctg                                                          10

<210> SEQ ID NO 17
<211> LENGTH: 10
<212> TYPE: DNA
<213> ORGANISM: Artificial
<220> FEATURE:
<223> OTHER INFORMATION: SAGE Tag

<400> SEQUENCE: 17
atcctgtagg                                                          10
```

METHODS FOR THE DIAGNOSIS AND TREATMENT OF LUNG CANCER

CROSS-REFERENCE TO RELATED APPLICATION

This application is a divisional of application Ser. No. 11/504,260, filed Aug. 14, 2006 (now abandoned), which is a continuation of application Ser. No. 09/646,478, filed Mar. 4, 2002 (now abandoned), which is a 371 of PCT/US99/06947, filed Mar. 30, 1999, which claims priority under 35 U.S.C. §119(e) to U.S. Provisional Application No. 60/080,044, filed Mar. 31, 1998, the contents of which are hereby incorporated by reference into the present disclosure.

TECHNICAL FIELD

This invention is in the field of cancer biology. In particular, the present invention provides compositions and methods for diagnosing and treating a neoplastic lung cell characterized by an overexpression of a proto-oncogene.

BACKGROUND

Despite numerous advances in medical research, cancer remains the second leading cause of death in the United States. In the industrialized nations, roughly one in five persons will die of cancer. Traditional modes of clinical care, such as surgical resection, radiotherapy and chemotherapy, have a significant failure rate, especially for solid tumors. Failure occurs either because the initial tumor is unresponsive, or because of recurrence due to regrowth at the original site and/or metastases.

Lung cancer is one of the most common malignancies worldwide and is the second leading cause of cancer death in man. See, American Cancer Society, Cancer facts and figures, 1996, Atlanta. Approximately 178,100 new cases of lung cancer were to be diagnosed in 1997, accounting for 13% of cancer diagnoses. An estimated 160,400 deaths due to lung cancer would occur in 1997 accounting for 29% of all cancer deaths. The one-year survival rates for lung cancer have increased from 32% in 1973 to 41% in 1993, largely due to improvements in surgical techniques. The 5 year survival rate for all stages combined is only 14%. The survival rate is 48% for cases detected when the disease is still localized, but only 15% of lung cancers are discovered that early. Among various forms of lung cancer, non-small cell lung cancer (NSCLC) accounts for nearly 80% of all new lung cancer cases each year. For patients diagnosed with NSCLC, surgical resection offers the only chance of meaningful survival. On the other hand, small cell lung cancer is the most malignant and fastest growing form of lung cancer and accounts for the rest of approximately 20% of new cases of lung cancer. The primary tumor is generally responsive to chemotherapy, but is followed by wide-spread metastasis. The median survival time at diagnosis is approximately 1 year, with a 5 year survival rate of 5%.

In spite of major advances in cancer therapy including improvements in surgical resection, radiation treatment and chemotherapy, successful intervention for lung cancer in particular, relies on early detection of the cancerous cells. Neoplasia resulting in benign tumors may be completely cured by removing the mass surgically. If a tumor becomes malignant, as manifested by invasion of surrounding tissue, it becomes much more difficult to eradicate. Therefore, there remains a considerable need in the art for the development of methods for detecting the disease at the early stage. There also exits a pressing need in the art for developing diagnostic methods to monitor or prognose the progression of the disease as well as methods to treat various conditions. However, the vast variability in the nature of the disease has rendered the search for cellular markers, such as genes that are preferably overexpressed in primary lung cancer cells and useful for diagnostic and therapeutic methods, difficult.

Tumor often results from genetic alterations occurring spontaneously, or from viral infection, or in response to chemical carcinogens or radiation. Genes responsible for transforming a normal cell to a cancer (or neoplastic) cell are known as oncogenes. With the advent of recombinant DNA technology, a large number of oncogenes have been identified, cloned and sequenced. In most cases, the identified oncogenes are in fact altered form of one of the same native cellular genes, known as the proto-oncogenes. Related techniques have revealed that cell transformation can also be caused by overproduction of certain normal gene products. Overexpression of proto-oncogene may result from an amplification of the gene copies, or from a chromosomal rearrangement that has brought the proto-oncogene under the control of an inappropriate regulatory element, such as a constitutively activated promoter. The present invention provides the first identification of proto-oncogenes that are preferably overexpressed in primary lung cancer cells. In addition, the methods described herein provide a significant contribution to the area of lung cancer diagnosis, monitoring and treatment.

DISCLOSURE OF THE INVENTION

The present invention provides methods for aiding in the diagnoses of the neoplastic condition of a lung cell, and methods of screening for a potential therapeutic agent for the reversal of the neoplastic condition.

Accordingly, one embodiment of this invention is a method of diagnosing the neoplastic condition of a lung cell by screening for the presence of an overexpressed proto-oncogene from a lung cell sample, in which the overexpression is indicative of the neoplastic state of the lung cell. In one aspect of this embodiment, the overexpressed proto-oncogene is b-myb or p67, and in another aspect, the overexpressed proto-oncogene is PGP9.5 or 8-oxo-dGTPase. The overexpression of the proto-oncogene embodied in the present invention is determined by detecting the quantity of mRNA transcribed from the proto-oncogene, or the quantity of cDNA produced from the reverse transcription of the mRNA, or the quantity of the polypeptide or protein encoded by the proto-oncogene. The methods are particularly useful for aiding in the diagnosis of non-small cell lung cancer.

Another embodiment of the invention is a screen for a potential therapeutic agent for the reversal of the neoplastic condition of a lung cell, wherein the cell is characterized by overexpression of a proto-oncogene. The method comprises contacting the cell with an effective amount of a potential agent and assaying for reversal of the neoplastic condition. In one aspect of this embodiment, the proto-oncogene is one or more of any of b-myb, p67, PGP9.5 or 8-oxo-dGTPase.

Yet another embodiment of the present invention is a method of reversing the neoplastic condition of a lung cell, wherein the cell is characterized by overexpression of a proto-oncogene by contacting the cell with an agent identified by the above-mentioned method. The identified agent can be, but is not limited to, anti-sense RNA that specifically inhibits the overexpression of the proto-oncogene. The overexpressed proto-oncogene is any of b-myb, p67, 8-oxo-dGTPase or PGP9.5.

MODES FOR CARRYING OUT THE INVENTION

Figure 1:
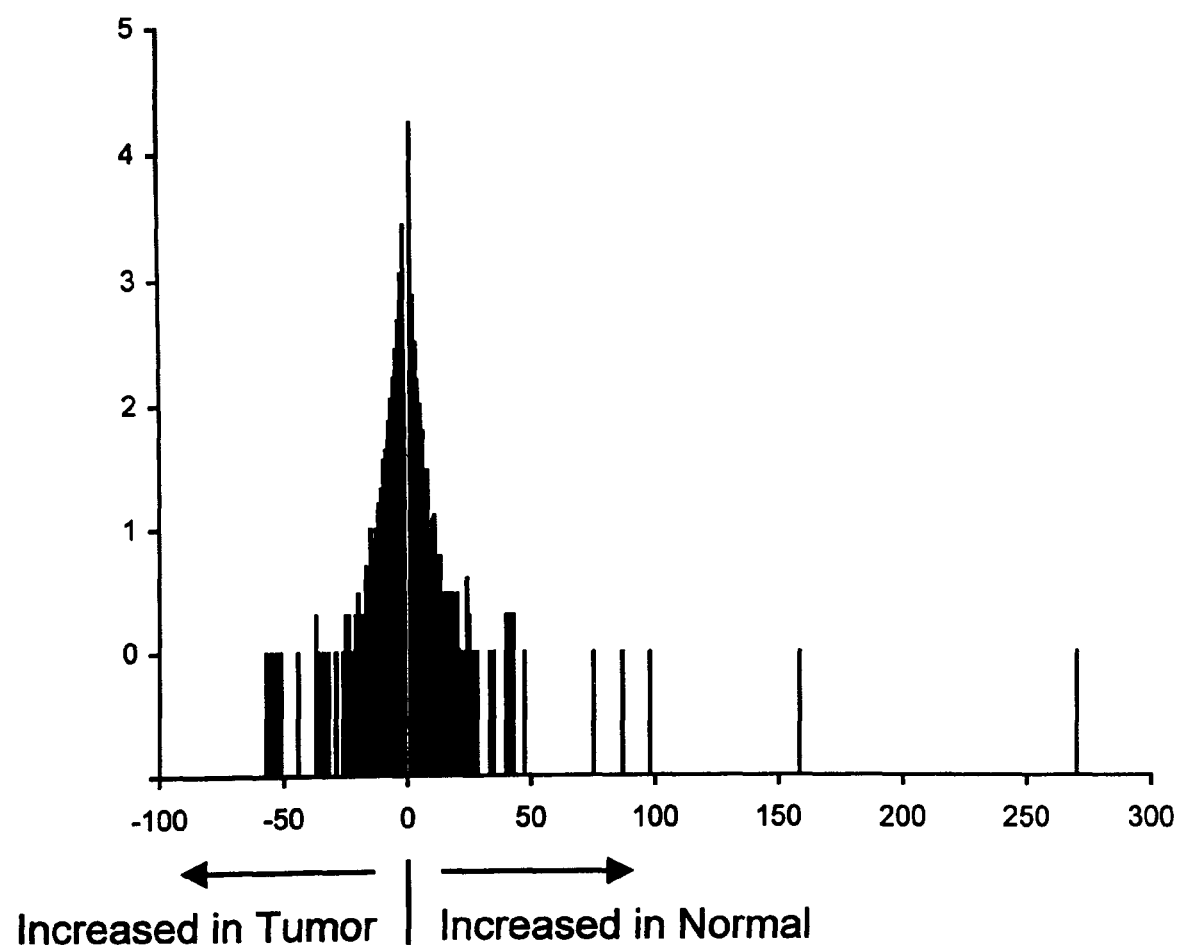
FIG. 1 depicts the relative expression of all unique tags in lung tumor and normal tissues. The ratio of tags present in the tumor and normal control was determined using the sum of the tags from each of the two libraries. In the case of a zero appearance, a number of 1 was inserted to allow the ratio to become a meaningful value. The x-axis indicates the fold induction in either system. A positive value indicates fold induction in the normal and a negative value indicate fold induction in the tumor. The y-axis indicates the number of genes differentially expressed where $y-10^n$.

Throughout this disclosure, various publications, patents and published patent specifications are referenced by an identifying citation. The disclosures of these publications, patents and published patent specifications are hereby incorporated by reference into the present disclosure to more fully describe the state of the art to which this invention pertains.

DEFINITIONS

The practice of the present invention will employ, unless otherwise indicated, conventional techniques of immunology, molecular biology, microbiology, cell biology and recombinant DNA, which are within the skill of the art. See, e.g., Sambrook, Fritsch and Maniatis, MOLECULAR CLONING: A LABORATORY MANUAL, $2^{nd}$ edition (1989); CURRENT PROTOCOLS IN MOLECULAR BIOLOGY (F. M. Ausubel, et al. eds., (1987)); the series METHODS IN ENZYMOLOGY (Academic Press, Inc.): PCR 2: A PRACTICAL APPROACH (M. J. MacPherson, B. D. Hames and G. R. Taylor eds. (1995)), Harlow and Lane, eds. (1988) ANTIBODIES, A LABORATORY MANUAL, and ANIMAL CELL CULTURE (R. I. Freshney, ed. (1987)).

As used in the specification and claims, the singular form "a", "an" and "the" include plural references unless the context clearly dictates otherwise. For example, the term "a cell" includes a plurality of cells, including mixtures thereof.

As used herein, the term "comprising" is intended to mean that the compositions and methods include the recited elements, but not excluding others. "Consisting essentially of" when used to define compositions and methods, shall mean excluding other elements of any essential significance to the combination. Thus, a composition consisting essentially of the elements as defined herein would not exclude trace contaminants from the isolation and purification method and pharmaceutically acceptable carriers, such as phosphate buffered saline, preservatives, and the like. "Consisting of" shall mean excluding more than trace elements of other ingredients and substantial method steps for administering the compositions of this invention. Embodiments defined by each of these transition terms are within the scope of this invention.

The term "polypeptide" is used in its broadest sense to refer to a compound of two or more subunit amino acids, amino acid analogs, or peptidomimetics. The subunits may be linked by peptide bonds. In another embodiment, the subunit may be linked by other bonds, e.g. ester, ether, etc. As used herein the term "amino acid" refers to either natural and/or unnatural or synthetic amino acids, including glycine and both the D or L optical isomers, and amino acid analogs and peptidomimetics. A peptide of three or more amino acids is commonly called an oligopeptide if the peptide chain is short. If the peptide chain is long, the peptide is commonly called a polypeptide or a protein.

The term "isolated" means separated from constituents, cellular and otherwise, in which the polynucleotide, peptide, polypeptide, protein, antibody, or fragments thereof, are normally associated with in nature. In one aspect of this invention, an isolated polynucleotide is separated from the 3' and 5' contiguous nucleotides with which it is normally associated with in its native or natural environment, e.g., on the chromosome. As is apparent to those of skill in the art, a non-naturally occurring polynucleotide, peptide, polypeptide, protein, antibody, or fragments thereof, does not require "isolation" to distinguish it from its naturally occurring counterpart. In addition, a "concentrated", "separated" or "diluted" polynucleotide, peptide, polypeptide, protein, antibody, or fragments thereof, is distinguishable from its naturally occurring counterpart in that the concentration or number of molecules per volume is greater than "concentrated" or less than "separated" than that of its naturally occurring counterpart. A polynucleotide, peptide, polypeptide, protein, antibody, or fragments thereof, which differs from the naturally occurring counterpart in its primary sequence or for example, by its glycosylation pattern, need not be present in its isolated form since it is distinguishable from its naturally occurring counterpart by its primary sequence, or alternatively, by another characteristic such as glycosylation pattern. Although not explicitly stated for each of the inventions disclosed herein, it is to be understood that all of the above embodiments for each of the compositions disclosed below and under the appropriate conditions, are provided by this invention. Thus, a non-naturally occurring polynucleotide is provided as a separate embodiment from the isolated naturally occurring polynucleotide. A protein produced in a bacterial cell is provided as a separate embodiment from the naturally occurring protein isolated from a eucaryotic cell in which it is produced in nature.

The terms "polynucleotide" and "oligonucleotide" are used interchangeably, and refer to a polymeric form of nucleotides of any length, either deoxyribonucleotides or ribonucleotides, or analogs thereof. Polynucleotides may have any three-dimensional structure, and may perform any function, known or unknown. The following are non-limiting examples of polynucleotides: a gene or gene fragment, exons, introns, messenger RNA (mRNA), transfer RNA, ribosomal RNA, ribozymes, cDNA, recombinant polynucleotides, branched polynucleotides, plasmids, vectors, isolated DNA of any sequence, isolated RNA of any sequence, nucleic acid probes, and primers. A polynucleotide may comprise modified nucleotides, such as methylated nucleotides and nucleotide analogs. If present, modifications to the nucleotide structure may be imparted before or after assembly of the polymer. The sequence of nucleotides may be interrupted by non-nucleotide components. A polynucleotide may be further modified after polymerization, such as by conjugation with a labeling component. The term also refers to both double- and single-stranded molecules. Unless otherwise specified or required, any embodiment of this invention that is a polynucleotide encompasses both the double-stranded form and each of two complementary single-stranded forms known or predicted to make up the double-stranded form.

A polynucleotide is composed of a specific sequence of four nucleotide bases: adenine (A); cytosine (C); guanine (G); thymine (T); and uracil (U) for thymine (T) when the polynucleotide is RNA. Thus, the term "polynucleotide sequence" is the alphabetical representation of a polynucleotide molecule. This alphabetical representation can be input into databases in a computer having a central processing unit and used for bioinformatics applications such as functional genomics and homology searching.

A "gene" refers to a polynucleotide containing at least one open reading frame that is capable of encoding a particular polypeptide or protein after being transcribed and translated. Any of the polynucleotides sequences described herein may be used to identify larger fragments or full-length coding sequences of the gene with which they are associated. Methods of isolating larger fragment sequences are known to those of skill in the art, some of which are described herein.

A "oncogene" refers to a polynucleotide containing at least one open reading frame, that is capable of transforming a normal cell to a cancerous (or neoplastic or tumor) cell when introduced into a host cell. Oncogenes are often altered forms of the cellular counterpart, namely the "proto-oncogenes" that are incapable of cell transformation when expressed at the level present in a non-cancer cell.

A "gene product" refers to the amino acid (e.g., peptide or polypeptide) generated when a gene is transcribed and translated.

As used herein a second polynucleotide "corresponds to" another (a first) polynucleotide if it is related to the first polynucleotide by any of the following relationships:
1) The second polynucleotide comprises the first polynucleotide and the second polynucleotide encodes a gene product.
2) The second polynucleotide is 5' or 3' to the first polynucleotide in cDNA, RNA, genomic DNA, or a fragment of any of these polynucleotides. For example, a second polynucleotide may be a fragment of a gene that includes the first and second polynucleotides. The first and second polynucleotides are related in that they are components of the gene coding for a gene product, such as a protein. However, it is not necessary that the second polynucleotide comprises or overlaps with the first polynucleotide to be "corresponding to" as used herein. For example, the first polynucleotide may be a fragment of a 3' untranslated region of the second polynucleotide. The first and second polynucleotide may be fragments of a gene coding for a gene product. The second polynucleotide may be an exon of the gene while the first polynucleotide may be an intron of the gene.
3) The second polynucleotide is the complement of the first polynucleotide.

A "probe" when used in the context of polynucleotide manipulation refers to an oligonucleotide that is provided as a reagent to detect a target potentially present in a sample of interest by hybridizing with the target. Usually, a probe will comprise a label or a means by which a label can be attached, either before or subsequent to the hybridization reaction. Suitable labels include, but are not limited to radioisotopes, fluorochromes, chemiluminescent compounds, dyes, and proteins, including enzymes.

A "primer" is a short polynucleotide, generally with a free 3'-OH group that binds to a target or "template" potentially present in a sample of interest by hybridizing with the target, and thereafter promoting polymerization of a polynucleotide complementary to the target. A "polymerase chain reaction" ("PCR") is a reaction in which replicate copies are made of a target polynucleotide using a "pair of primers" or a "set of primers" consisting of an "upstream" and a "downstream" primer, and a catalyst of polymerization, such as a DNA polymerase, and typically a thermally-stable polymerase enzyme. Methods for PCR are well known in the art, and taught, for example in "PCR: A PRACTICAL APPROACH" (M. MacPherson et al., IRL Press at Oxford University Press (1991)). All processes of producing replicate copies of a polynucleotide, such as PCR or gene cloning, are collectively referred to herein as "replication." A primer can also be used as a probe in hybridization reactions, such as Southern or Northern blot analyses. Sambrook et al., supra.

A "sequence tag" or "SAGE tag" is a short sequence, generally under about 20 nucleotides, that occurs in a certain position in messenger RNA. The tag can be used to identify the corresponding transcript and gene from which it was transcribed. A "ditag" is a dimer of two sequence tags.

An expression "database" denotes a set of stored data that represent a collection of sequences, which in turn represent a collection of biological reference materials.

The term "cDNAs" refers to complementary DNA, that is mRNA molecules present in a cell or organism made in to cDNA with an enzyme such as reverse transcriptase. A "cDNA library" is a collection of all of the mRNA molecules present in a cell or organism, all turned into cDNA molecules with the enzyme reverse transcriptase, then inserted into "vectors" (other DNA molecules that can continue to replicate after addition of foreign DNA). Exemplary vectors for libraries include bacteriophage (also known as "phage"), viruses that infect bacteria, for example, lambda phage. The library can then be probed for the specific cDNA (and thus mRNA) of interest.

"Differentially expressed" as applied to a gene, refers to the differential production of the mRNA transcribed from the gene or the protein product encoded by the gene. A differentially expressed gene may be overexpressed or underexpressed as compared to the expression level of a normal or control cell. In one aspect, it refers to a differential that is 2.5 times, preferably 5 times, or preferably 10 times higher or lower than the expression level detected in a control sample. The term "differentially expressed" also refers to nucleotide sequences in a cell or tissue which are expressed where silent in a control cell or not expressed where expressed in a control cell.

The term "anti-sense RNA" or "asRNA" refers to an RNA molecule having a nucleotide sequence that is complementary to a specific mRNA sequence. Antisense RNA can be synthesized by methods known in the art, for example by splicing the gene of interest in a reverse orientation to a viral promoter so that the coding strand is transcribed. (see, Armentano et al. (1987) J. Virol. 61:1647-1650 for discussion of one suitable promoter). The isolated asRNA produced by the vector can then be introduced into an organism where it combines with naturally occurring mRNA to form duplexes which block either further transcription or translation. Methods of introducing asRNA into cells include, but are not limited to, non-toxic cationic lipids as described in Chiang et al. (1991) J. Biol. Chem. 266:18162-18171. A review of anti-sense therapy can be found in C. A. Stein (1999) Nature Biotech. 17(3):209.

As used herein, "solid phase support" or "solid support", used interchangeably, is not limited to a specific type of support. Rather a large number of supports are available and are known to one of ordinary skill in the art. Solid phase supports include silica gels, resins, derivatized plastic films, glass beads, cotton, plastic beads, alumina gels. As used herein, "solid support" also includes synthetic antigen-presenting matrices, cells, and liposomes. A suitable solid phase support may be selected on the basis of desired end use and suitability for various protocols. For example, for peptide synthesis, solid phase support may refer to resins such as polystyrene (e.g., PAM-resin obtained from Bachem Inc., Peninsula Laboratories, etc.), POLYHIPE® resin (obtained from Aminotech, Canada), polyamide resin (obtained from Peninsula Laboratories), polystyrene resin grafted with polyethylene glycol (TentaGel®, Rapp Polymere, Tubingen, Germany) or polydimethylacrylamide resin (obtained from Milligen/Biosearch, California).

A polynucleotide also can be attached to a solid support for use in high throughput screening assays. PCT WO 97/10365, for example, discloses the construction of high density oligonucleotide chips. See also, U.S. Pat. Nos. 5,405,783; 5,412, 087; and 5,445,934. Using this method, the probes are synthesized on a derivatized glass surface also known as chip arrays. Photoprotected nucleoside phosphoramidites are coupled to the glass surface, selectively deprotected by photolysis through a photolithographic mask, and reacted with a second protected nucleoside phosphoramidite. The coupling/deprotection process is repeated until the desired probe is complete.

As used herein, "expression" refers to the process by which polynucleotides are transcribed into mRNA and/or the process by which the transcribed mRNA is subsequently being translated into peptides, polypeptides, or proteins. If the polynucleotide is derived from genomic DNA, expression may include splicing of the mRNA in an eukaryotic cell.

"Overexpression" as applied to a gene, refers to the overproduction of the mRNA transcribed from the gene or the protein product encoded by the gene, at a level that is 2.5 times higher, preferably 5 times higher, more preferably 10 times higher than the expression level detected in a control sample.

"Hybridization" refers to a reaction in which one or more polynucleotides react to form a complex that is stabilized via hydrogen bonding between the bases of the nucleotide residues. The hydrogen bonding may occur by Watson-Crick base pairing, Hoogstein binding, or in any other sequence-specific manner. The complex may comprise two strands forming a duplex structure, three or more strands forming a multi-stranded complex, a single self-hybridizing strand, or any combination of these. A hybridization reaction may constitute a step in a more extensive process, such as the initiation of a PCR reaction, or the enzymatic cleavage of a polynucleotide by a ribozyme.

Hybridization reactions can be performed under conditions of different "stringency". In general, a low stringency hybridization reaction is carried out at about 40° C. in 10×SSC or a solution of equivalent ionic strength/temperature. A moderate stringency hybridization is typically performed at about 50° C. in 6×SSC, and a high stringency hybridization reaction is generally performed at about 60° C. in 1×SSC.

When hybridization occurs in an antiparallel configuration between two single-stranded polynucleotides, the reaction is called "annealing" and those polynucleotides are described as "complementary". A double-stranded polynucleotide can be "complementary" or "homologous" to another polynucleotide, if hybridization can occur between one of the strands of the first polynucleotide and the second. "Complementarity" or "homology" (the degree that one polynucleotide is complementary with another) is quantifiable in terms of the proportion of bases in opposing strands that are expected to form hydrogen bonding with each other, according to generally accepted base-pairing rules.

A polynucleotide or polynucleotide region (or a polypeptide or polypeptide region) has a certain percentage (for example, 80%, 85%, 90%, or 95%) of "sequence identity" to another sequence means that, when aligned, that percentage of bases (or amino acids) are the same in comparing the two sequences. This alignment and the percent homology or sequence identity can be determined using software programs known in the art, for example those described in CURRENT PROTOCOLS IN MOLECULAR BIOLOGY (F. M. Ausubel et al., eds., 1987) Supplement 30, section 7.7.18, Table 7.7.1. Preferably, default parameters are used for alignment. A preferred alignment program is BLAST, using default parameters. In particular, preferred programs are BLASTN and BLASTP, using the following default parameters: Genetic code=standard; filter=none; strand=both; cutoff=60; expect=10; Matrix=BLOSUM62; Descriptions=50 sequences; sort by =HIGH SCORE; Databases=non-redundant, GenBank+EMBL+DDBJ+PDB+GenBank CDS translations+SwissProtein+SPupdate+PIR. Details of these programs can be found at the following Internet address: http://www.ncbi.nlm.nih.gov/cgi-bin/BLAST.

As used herein, the terms "neoplastic cells", "neoplasia", "tumor", "tumor cells", "cancer" and "cancer cells", (used interchangeably) refer to cells which exhibit relatively autonomous growth, so that they exhibit an aberrant growth phenotype characterized by a significant loss of control of cell proliferation (i.e., de-regulated cell division). Neoplastic cells can be malignant or benign. A metastatic cell or tissue means that the cell can invade and destroy neighboring body structures.

"Suppressing" tumor growth indicates a growth state that is curtailed when compared to growth without contact with educated, antigen-specific immune effector cells described herein. Tumor cell growth can be assessed by any means known in the art, including, but not limited to, measuring tumor size, determining whether tumor cells are proliferating using a $^3$H-thymidine incorporation assay, or counting tumor cells.

"Suppressing" tumor cell growth means any or all of the following states: slowing, delaying, and stopping tumor growth, as well as tumor shrinkage.

Hyperplasia is a form of controlled cell proliferation involving an increase in cell number in a tissue or organ, without significant alteration in structure or function. Metaplasia is a form of controlled cell growth in which one type of fully differentiated cell substitutes for another type of differentiated cell. Metaplasia can occur in epithelial or connective tissue cells. Atypical metaplasia involves a somewhat disorderly metaplastic epithelium.

A "composition" is intended to mean a combination of active agent and another compound or composition, inert (for example, a detectable agent or label) or active, such as an adjuvant.

A "pharmaceutical composition" is intended to include the combination of an active agent with a carrier, inert or active, making the composition suitable for diagnostic or therapeutic use in vitro, in vivo or ex vivo.

As used herein, the term "pharmaceutically acceptable carrier" encompasses any of the standard pharmaceutical carriers, such as a phosphate buffered saline solution, water, and emulsions, such as an oil/water or water/oil emulsion, and various types of wetting agents. The compositions also can include stabilizers and preservatives. For examples of carriers, stabilizers and adjuvants, see Martin, REMINGTON'PHARM. SCI., 15th Ed. (Mack Publ. Co., Easton (1975)).

An "effective amount" is an amount sufficient to effect beneficial or desired results. An effective amount can be administered in one or more administrations, applications or dosages.

A "subject," "individual" or "patient" is used interchangeably herein, which refers to a vertebrate, preferably a mammal, more preferably a human. Mammals include, but are not limited to, murines, simians, humans, farm animals, sport animals, and pets.

A "control" is an alternative subject or sample used in an experiment for comparison purpose. A control can be "positive" or "negative". For example, where the purpose of the experiment is to determine a correlation of an altered expression level of a proto-oncogene with a particular type of cancer, it is generally preferable to use a positive control (a subject or a sample from a subject, carrying such alteration and exhibiting syndromes characteristic of that disease), and a negative control (a subject or a sample from a subject lacking the altered expression and clinical syndrome of that disease).

As noted above, this invention provides various methods for aiding in the diagnosis of the neoplastic state of a lung cell that is characterized by abnormal cell growth in the form of, e.g., malignancy, hyperplasia or metaplasia. The neoplastic state of a cell generally is determined by noting whether the growth of the cell is not governed by the usual limitation of normal growth. For the purposes of this invention, the term also is to include genotypic changes that occur prior to detection of this growth in the form of a tumor and are causative of these phenotypic changes. The phenotypic changes associated with the neoplastic state of a cell (a set of in vitro characteristics associated with a tumorigenic ability in vivo) include a more rounded cell morphology, looser substratum attachment, loss of contact inhibition, loss of anchorage dependence, release of proteases such as plasminogen activator, increased sugar transport, decreased serum requirement, expression of fetal antigens and the like. (See Luria, et al. (1978) GENERAL VIROLOGY, $3^d$ edition, 436-446 (John Wiley & Sons, New York)).

The cell of this invention is characterized by overexpression of a proto-oncogene selected from the group of proto-oncogenes 8-oxo-dGTPase, b-myb, p67, or PGP9.5. In one embodiment, overexpression is determined by assaying for the expression of the gene in the test system and its absence in the control. In one embodiment, overexpression is determined by an increase by 2.5 fold, preferably 5 fold, more preferably 10 fold in the level of proto-oncogene mRNA. In a separate embodiment, an augmentation in the level of the polypeptide or protein encoded by the proto-oncogene is indicative of the presence of the neoplastic condition of the cell. The method can be used for aiding in the diagnosis of a lung cancer such as non-small cell lung cancer by detecting a genotype that is correlated with a phenotype characteristic of primary lung tumor cells. Thus, by detecting this genotype prior to tumor growth, one can predict a predisposition to cancer or provide early diagnosis.

Cell or tissue samples used for this invention encompass body fluid, solid tissue samples, tissue cultures or cells derived therefrom and the progeny thereof, and sections or smears prepared from any of these sources, or any other samples that may contain a lung cell having a proto-oncogenes b-myb, 8-oxo-dGTPase, p67 or PGP9.5 or their gene products. A preferred sample is one that is prepared from a subject's lung tissue.

In assaying for an alteration in mRNA level, nucleic acid contained in the aforementioned samples is first extracted according to standard methods in the art. For instance, mRNA can be isolated using various lytic enzymes or chemical solutions according to the procedures set forth in Sambrook et al. (1989), supra or extracted by nucleic-acid-binding resins following the accompanying instructions provided by manufactures. The mRNA of a proto-oncogene of interest contained in the extracted nucleic acid sample is then detected by hybridization (e.g. Northern blot analysis) and/or amplification procedures according to methods widely known in the art or based on the methods exemplified herein.

Nucleic acid molecules having at least 10 nucleotides and exhibiting sequence complementarity or homology to the proto-oncogenes described herein find utility as hybridization probes. It is known in the art that a "perfectly matched" probe is not needed for a specific hybridization. Minor changes in probe sequence achieved by substitution, deletion or insertion of a small number of bases do not affect the hybridization specificity. In general, as much as 20% base-pair mismatch (when optimally aligned) can be tolerated. Preferably, a probe useful for detecting the aforementioned proto-oncogene mRNA is at least about 80% identical to the homologous region of comparable size contained in the previously identified sequences, which have the GenBank accession numbers identified in Table 2 (below). More preferably, the probe is 85% identical to the corresponding gene sequence after alignment of the homologous region; even more preferably, it exhibits 90% identity. Specifically, a preferred probe for b-myb is TGCTGCCCTG (SEQ ID NO. 1), a preferred probe for PGP9.5 is CAGTCTAAAA (SEQ ID NO. 2), a preferred probe for 8-oxo-dGTPase is TGGCCCGACG (SEQ ID NO. 3), and a preferred probe for p67 is TAATACTTTT (SEQ ID NO. 4), or their respective complements Additional probes can be derived from sequences for these genes identified by the GenBank Accession numbers provided in Table 2 or to a homologous region of comparable size contained in the previously identified sequences, which have the GenBank accession numbers identified in Table 2. These probes can be used in radioassays (e.g. Southern and Northern blot analysis) to detect, prognose, diagnose or monitor various neoplastic states resulting from overexpression of PGP9.5, p67, 8-oxo-dGTPase or the b-myb genes. The total size of fragment, as well as the size of the complementary stretches, will depend on the intended use or application of the particular nucleic acid segment. Smaller fragments derived from the known sequences will generally find use in hybridization embodiments, wherein the length of the complementary region may be varied, such as between about 10 and about 100 nucleotides, or even full length according to the complementary sequences one wishes to detect.

Nucleotide probes having complementary sequences over stretches greater than about 10 nucleotides in length are generally preferred, so as to increase stability and selectivity of the hybrid, and thereby improving the specificity of particular hybrid molecules obtained. More preferably, one can design nucleic acid molecules having gene-complementary stretches of more than about 25 and even more preferably more than about 50 nucleotides in length, or even longer where desired.

Such fragments may be readily prepared by, for example, directly synthesizing the fragment by chemical means, by application of nucleic acid reproduction technology, such as the PCR™ technology with two priming oligonucleotides as described in U.S. Pat. No. 4,603,102 or by introducing selected sequences into recombinant vectors for recombinant production. A preferred probe is about 50 to about 75 or more preferably, about 50 to about 100, nucleotides in length.

In certain embodiments, it will be advantageous to employ nucleic acid sequences of the present invention in combination with an appropriate means, such as a label, for detecting hybridization and therefore complementary sequences. A wide variety of appropriate indicator means are known in the art, including fluorescent, radioactive, enzymatic or other ligands, such as avidin/biotin, which are capable of giving a detectable signal. In preferred embodiments, one will likely desire to employ a fluorescent label or an enzyme tag, such as urease, alkaline phosphatase or peroxidase, instead of radioactive or other environmental undesirable reagents. In the case of enzyme tags, colorimetric indicator substrates are known which can be employed to provide a means visible to the human eye or spectrophotometrically, to identify specific hybridization with complementary nucleic acid-containing samples.

Hybridization reactions can be performed under conditions of different "stringency". Relevant conditions include temperature, ionic strength, time of incubation, the presence of additional solutes in the reaction mixture such as formamide, and the washing procedure. Higher stringency conditions are those conditions, such as higher temperature and lower sodium ion concentration, which require higher minimum complementarity between hybridizing elements for a stable hybridization complex to form. Conditions that increase the stringency of a hybridization reaction are widely known and published in the art. See, for example, (Sambrook, et al., (1989), supra).

Briefly, multiple RNAs are isolated from cell or tissue samples as described above. Optionally, the gene transcripts can be converted to cDNA. A sampling of the gene transcripts are subjected to sequence-specific analysis and quantified. These gene transcript sequence abundances are compared against reference database sequence abundances including normal data sets for diseased and healthy patients. The patient has the disease(s) with which the patient's data set most closely correlates which includes the overexpression of the transcripts identified herein.

The nucleotide probes of the present invention can also be used as primers and detection of genes or gene transcripts that are differentially expressed in certain body tissues. A preferred primer for b-myb is TGCTGCCCTG (SEQ ID NO. 1), the preferred primer for PGP9.5 is CAGTCTAAAA (SEQ ID NO. 2), the preferred primer for 8-oxo-dGTPase is TGGC-CCGACG (SEQ ID NO. 3), and a preferred probe is TAATACTTTT (SEQ ID NO. 4), or their respective complements. Additionally, a primer useful for detecting the aforementioned proto-oncogene mRNA is at least about 80% identical to the homologous region of comparable size contained in the previously identified sequences, which have the GenBank accession numbers identified in Table 2. For the purpose of this invention, amplification means any method employing a primer-dependent polymerase capable of replicating a target sequence with reasonable fidelity. Amplification may be carried out by natural or recombinant DNA-polymerases such as T7 DNA polymerase, Klenow fragment of *E. coli* DNA polymerase, and reverse transcriptase.

A preferred amplification method is PCR. General procedures for PCR are taught in MacPherson et al., PCR: A PRACTICAL APPROACH, (IRL Press at Oxford University Press (1991)). However, PCR conditions used for each application reaction are empirically determined. A number of parameters influence the success of a reaction. Among them are annealing temperature and time, extension time, $Mg^{2+}$ ATP concentration, pH, and the relative concentration of primers, templates, and deoxyribonucleotides.

After amplification, the resulting DNA fragments can be detected by agarose gel electrophoresis followed by visualization with ethidium bromide staining and ultraviolet illumination. A specific amplification of proto-oncogenes such as GPG9.5, p67, 8-oxo-dGTPase or b-myb can be verified by demonstrating that the amplified DNA fragment has the predicted size, exhibits the predicated restriction digestion pattern, and/or hybridizes to the correct cloned DNA sequence.

The probes also can be attached to a solid support for use in high throughput screening assays using methods known in the art. PCT WO 97/10365 and U.S. Pat. Nos. 5,405,783, 5,412,087 and 5,445,934, for example, disclose the construction of high density oligonucleotide chips which can contain one or more of the sequences disclosed herein. Using the methods disclosed in U.S. Pat. Nos. 5,405,783, 5,412,087 and 5,445,934 the probes of this invention are synthesized on a derivatized glass surface. Photoprotected nucleoside phosphoramidites are coupled to the glass surface, selectively deprotected by photolysis through a photolithographic mask, and reacted with a second protected nucleoside phosphoramidite. The coupling/deprotection process is repeated until the desired probe is complete.

The expression level of a proto-oncogene is determined through exposure of a nucleic acid sample to the probe-modified chip. Extracted nucleic acid is labeled, for example, with a fluorescent tag, preferably during an amplification step. Hybridization of the labeled sample is performed at an appropriate stringency level. The degree of probe-nucleic acid hybridization is quantitatively measured using a detection device, such as a confocal microscope. See U.S. Pat. Nos. 5,578,832 and 5,631,734. The obtained measurement is directly correlated with proto-oncogene expression level.

More specifically, the probes and high density oligonucleotide probe arrays provide an effective means of monitoring expression of a multiplicity of genes. The expression monitoring methods of this invention may be used in a wide variety of circumstances including detection of disease, identification of differential gene expression between two samples, or screening for compositions that upregulate or downregulate the expression of particular genes.

In another preferred embodiment, the methods of this invention are used to monitor expression of the genes which specifically hybridize to the probes of this invention in response to defined stimuli, such as a drug.

In one embodiment, the hybridized nucleic acids are detected by detecting one or more labels attached to the sample nucleic acids. The labels may be incorporated by any of a number of means well known to those of skill in the art. However, in one aspect, the label is simultaneously incorporated during the amplification step in the preparation of the sample nucleic acid. Thus, for example, polymerase chain reaction (PCR) with labeled primers or labeled nucleotides will provide a labeled amplification product. In a separate embodiment, transcription amplification, as described above, using a labeled nucleotide (e.g. fluorescein-labeled UTP and/or CTP) incorporates a label in to the transcribed nucleic acids.

Alternatively, a label may be added directly to the original nucleic acid sample (e.g., mRNA, polyA, mRNA, cDNA, etc.) or to the amplification product after the amplification is completed. Means of attaching labels to nucleic acids are well known to those of skill in the art and include, for example nick translation or end-labeling (e.g. with a labeled RNA) by kinasing of the nucleic acid and subsequent attachment (ligation) of a nucleic acid linker joining the sample nucleic acid to a label (e.g., a fluorophore).

Detectable labels suitable for use in the present invention include any composition detectable by spectroscopic, photochemical, biochemical, immunochemical, electrical, optical or chemical means. Useful labels in the present invention include biotin for staining with labeled streptavidin conjugate, magnetic beads (e.g., Dynabeads™), fluorescent dyes (e.g., fluorescein, texas red, rhodamine, green fluorescent protein, and the like), radiolabels (e.g., $^3H$, $^{125}I$, $^{35}S$, $^{14}C$, or $^{32}P$) enzymes (e.g., horse radish peroxidase, alkaline phosphatase and others commonly used in an ELISA), and colorimetric labels such as colloidal gold or colored glass or plastic (e.g., polystyrene, polypropylene, latex, etc.) beads. Patents teaching the use of such labels include U.S. Pat. Nos. 3,817,837; 3,850,752; 3,939,350; 3,996,345; 4,277,437; 4,275,149; and 4,366,241).

Means of detecting such labels are well known to those of skill in the art. Thus, for example, radiolabels may be detected using photographic film or scintillation counters, fluorescent markers may be detected using a photodetector to detect emitted light. Enzymatic labels are typically detected by providing the enzyme with a substrate and detecting the reaction product produced by the action of the enzyme on the substrate, and colorimetric labels are detected by simply visualizing the colored label.

As described in more detail in WO 97/10365, the label may be added to the target (sample) nucleic acid(s) prior to, or after the hybridization. These are detectable labels that are directly attached to or incorporated into the target (sample) nucleic acid prior to hybridization. In contrast, "indirect labels" are joined to the hybrid duplex after hybridization. Often, the indirect label is attached to a binding moiety that has been attached to the target nucleic acid prior to the hybridization. Thus, for example, the target nucleic acid may be biotinylated before the hybridization. After hybridization, an aviden-conjugated fluorophore will bind the biotin bearing hybrid duplexes providing a label that is easily detected. Fore a detailed review of methods of labeling nucleic acids and detecting labeled hybridized nucleic acids see LABORATORY TECHNIQUES IN BIOCHEMISTRY AND MOLECULAR BIOLOGY, Vol. 24: Hybridization with Nucleic Acid Probes, P. Tijssen, ed. Elsevier, N.Y. (1993).

The nucleic acid sample also may be modified prior to hybridization to the high density probe array in order to reduce sample complexity thereby decreasing background signal and improving sensitivity of the measurement using the methods disclosed in WO 97/10365.

Results from the chip assay are typically analyzed using a computer software program. See, for example, EP 0717 113 A2 and WO 95/20681. The hybridization data is read into the program, which calculates the expression level of the targeted gene(s). This figure is compared against existing data sets of gene expression levels for diseased and healthy individuals. A correlation between the obtained data and that of a set of diseased individuals indicates the onset of a disease in the subject patient.

Also within the scope of this application is a data base useful for the detection of neoplastic lung tissue comprising one or more of the sequences identified herein as Sequence ID Nos. 1 through 4 or parts of the Sequences identified in Table 2, below.

These polynucleotide sequences are stored in a digital storage medium such that a data processing system for standardized representation of the genes that identify a lung cancer cell is compiled. The data processing system is useful to analyze gene expression between two cells by first selecting a cell suspected of being of a neoplastic phenotype or genotype and then isolating polynucleotides from the cell. The isolated polynucleotides are sequenced. The sequences from the sample are compared with the sequence(s) present in the database using homology search techniques described above. Greater than 90%, more preferably greater than 95% and more preferably, greater than or equal to 97% sequence identity between the test sequence and at least one sequence identified by SEQ ID NO. 1 through 40 or its complement is a positive indication that the polynucleotide has been isolated from a lung cancer cell as defined above.

Expression of the proto-oncogenes PGP9.5, p67, 8-oxo-dGTPase and b-myb genes can also be determined by examining the protein product. Determining the protein level involves a) providing a biological sample containing polypeptides; and (b) measuring the amount of any immunospecific binding that occurs between an antibody reactive to PGP9.5, p67, 8-oxo-dGTPase or b-myb proteins and a component in the sample, in which the amount of immunospecific binding indicates the level of the proto-oncogene proteins.

Antibodies that specifically recognize and bind to the protein products of these proto-oncogenes are required for immunoassays. These may be purchased from commercial vendors or generated and screened using methods well known in the art. See Harlow and Lane (1988) supra. and Sambrook et al. (1989) supra.

A variety of techniques are available in the art for protein analysis. They include but are not limited to radioimmunoassays, ELISA (enzyme linked immunoradiometric assays), "sandwich" immunoassays, immunoradiometric assays, in situ immunoassays (using e.g., colloidal gold, enzyme or radioisotope labels), western blot analysis, immunoprecipitation assays, immunoflourescent assays, and PAGE-SDS.

In diagnosing malignancy, hyperplasia or metaplasia characterized by a differential expression of proto-oncogenes, one typically conducts a comparative analysis of the subject and appropriate controls. Preferably, a diagnostic test includes a control sample derived from a subject (hereinafter "positive control"), that exhibits a detectable increase in proto-oncogene expression, preferably at a level of at least 2.5 fold and clinical characteristics of the malignancy or metaplasia of interest. More preferably, a diagnosis also includes a control sample derived from a subject (hereinafter "negative control"), that lacks the clinical characteristics of the neoplastic state and whose expression level of the gene at question is within a normal range. A positive correlation between the subject and the positive control with respect to the identified alterations indicates the presence of or a predisposition to said disease. A lack of correlation between the subject and the negative control confirms the diagnosis. In a preferred embodiment, the method is used for diagnosing lung cancer, preferably non-small lung cancer, on the basis of an increase in PGP9.5, 8-oxo-dGTPase or b-myb mRNA level or protein level.

There are various methods available in the art for quantifying mRNA or protein level from a cell sample and indeed, any method that can quantify these levels is encompassed by this invention. For example, determination of the mRNA level of the aforementioned proto-oncogenes may involve, in one aspect, measuring the amount of mRNA in a mRNA sample isolated from the lung cell by hybridization or quantitative amplification using at least one oligonucleotide probe that is complementary to the mRNA. Determination of the aforementioned proto-oncogene products requires measuring the amount of immunospecific binding that occurs between an antibody reactive to the gene product of the proto-oncogene. To detect and quantify the immunospecific binding, or signals generated during hybridization or amplification procedures, digital image analysis systems including but not limited to those that detect radioactivity of the probes or chemiluminescence can be employed.

The present invention also provides a screen for various agents and methods for reversing the neoplastic condition of the cells or selectively inhibiting growth or proliferation of the cells described above. In one aspect, the screen assays for agents which are useful for the treatment of malignancy, hyperplasia or metaplasia characterized by overexpression of the proto-oncogenes.

Thus, to practice the method in vitro, suitable cell cultures or tissue cultures are first provided. The cell can be a cultured cell or a genetically modified cell which overexpresses a proto-oncogene associated with a neoplastic lung cell such as b-myb, p67, 8-oxo-dGTPase or PGP9.5. Alternatively, the cells can be from a tissue biopsy. The cells are cultured under conditions (temperature, growth or culture medium and gas ($CO_2$)) and for an appropriate amount of time to attain exponential proliferation without density dependent constraints. It also is desirable to maintain an additional separate cell culture; one which does not receive the agent being tested as a control.

As is apparent to one of skill in the art, suitable cells may be cultured in microtiter plates and several agents may be assayed at the same time by noting genotypic changes, phenotypic changes and/or cell death.

When the agent is a composition other than a DNA or RNA nucleic acid molecule, the suitable conditions may be by directly added to the cell culture or added to culture medium for addition. As is apparent to those skilled in the art, an "effective" amount must be added which can be empirically determined.

The screen involves contacting the agent with a test cell characterized by overexpression of these proto-oncogenes and then assaying the cell for the level of proto-oncogene expression. In some aspects, it may be necessary to determine the level of proto-oncogene expression prior to the assay. This provides a base line to compare expression after administration of the agent to the cell culture. In another embodiment, the test cell is a cultured cell from an established cell line that constitutively overexpresses these proto-oncogenes. Examples of these cell lines include, but are not limited the cell lines identified below. An agent is a possible therapeutic agent if the proto-oncogene expression is reduced to a level that is present in a cell in a normal or non-neoplastic state, or the cell selectively dies, or exhibits reduced rate of growth.

For the purposes of this invention, an "agent" is intended to include, but not be limited to a biological or chemical compound such as a simple or complex organic or inorganic molecule, a peptide, a protein or an oligonucleotide. A vast array of compounds can be synthesized, for example oligomers, such as oligopeptides and oligonucleotides, and synthetic organic compounds based on various core structures, and these are also included in the term "agent". In addition, various natural sources can provide compounds for screening, such as plant or animal extracts, and the like. It should be understood, although not always explicitly stated that the agent is used alone or in combination with another agent, having the same or different biological activity as the agents identified by the inventive screen. The agents and methods also are intended to be combined with other therapies.

As used herein, the term "reversing the neoplastic state of the cell" is intended to include apoptosis, necrosis or any other means of preventing cell division, reduced tumorigenicity, loss of pharmaceutical resistance, maturation, differentiation or reversion of the neoplastic phenotypes as described herein. As noted above, lung cells having overexpression of a proto-oncogene that results in the neoplastic state are suitably treated by this method. These cells can be identified by any method known in the art that allows for the identification of overexpression of the proto-oncogene. One such method is exemplified below.

When the agent is a nucleic acid, it can be added to the cell cultures by methods well known in the art, which includes, but is not limited to calcium phosphate precipitation, microinjection or electroporation. Alternatively or additionally, the nucleic acid can be incorporated into an expression or insertion vector for incorporation into the cells. Vectors that contain both a promoter and a cloning site into which a polynucleotide can be operatively linked are well known in the art. Such vectors are capable of transcribing RNA in vitro or in vivo, and are commercially available from sources such as Stratagene (La Jolla, Calif.) and Promega Biotech (Madison, Wis.). In order to optimize expression and/or in vitro transcription, it may be necessary to remove, add or alter 5' and/or 3' untranslated portions of the clones to eliminate extra, potential inappropriate alternative translation initiation codons or other sequences that may interfere with or reduce expression, either at the level of transcription or translation. Alternatively, consensus ribosome binding sites can be inserted immediately 5' of the start codon to enhance expression. Examples of vectors are viruses, such as baculovirus and retrovirus, bacteriophage, adenovirus, adeno-associated virus, cosmid, plasmid, fungal vectors and other recombination vehicles typically used in the art which have been described for expression in a variety of eukaryotic and prokaryotic hosts, and may be used for gene therapy as well as for simple protein expression.

Among these are several non-viral vectors, including DNA/liposome complexes, and targeted viral protein DNA complexes. To enhance delivery to a cell, the nucleic acid or proteins of this invention can be conjugated to antibodies or binding fragments thereof which bind cell surface antigens. Liposomes that also comprise a targeting antibody or fragment thereof can be used in the methods of this invention. This invention also provides the targeting complexes for use in the methods disclosed herein.

Polynucleotides are inserted into vector genomes using methods well known in the art. For example, insert and vector DNA can be contacted, under suitable conditions, with a restriction enzyme to create complementary ends on each molecule that can pair with each other and be joined together with a ligase. Alternatively, synthetic nucleic acid linkers can be ligated to the termini of restricted polynucleotide. These synthetic linkers contain nucleic acid sequences that correspond to a particular restriction site in the vector DNA. Additionally, an oligonucleotide containing a termination codon and an appropriate restriction site can be ligated for insertion into a vector containing, for example, some or all of the following: a selectable marker gene, such as the neomycin gene for selection of stable or transient transfectants in mammalian cells; enhancer/promoter sequences from the immediate early gene of human CMV for high levels of transcription; transcription termination and RNA processing signals from SV40 for mRNA stability; SV40 polyoma origins of replication and ColE1 for proper episomal replication; versatile multiple cloning sites; and T7 and SP6 RNA promoters for in vitro transcription of sense and antisense RNA. Other means are well known and available in the art.

One can determine if the object of the method, i.e., reversal of the neoplastic state of the cell, has been achieved by a reduction of cell division, differentiation of the cell or assaying for a reduction in proto-oncogene overexpression. Cellular differentiation can be monitored by histological methods or by monitoring for the presence or loss of certain cell surface markers, which may be associated with an undifferentiated phenotype, e.g. CD34 on primitive hematopoietic stem cells.

Kits containing the agents and instructions necessary to perform the screen and in vitro method as described herein also are claimed.

When the subject is an animal such as a rat or mouse, the method provides a convenient animal model system which can be used prior to clinical testing of the therapeutic agent. In this system, a candidate agent is a potential drug if proto-oncogene expression is reduced in a neoplastic lung cell or if symptoms associated or correlated to the presence of cells containing proto-oncogene overexpression are ameliorated, each as compared to untreated, animal having the pathological cells. It also can be useful to have a separate negative control group of cells or animals which are healthy and not treated, which provides a basis for comparison.

These agents of this invention and the above noted compounds and their derivatives may be used for the preparation of medicaments for use in the methods described herein.

In a preferred embodiment, an agent of the invention is administered to treat lung cancer. In a further preferred embodiment, an agent of the invention is administered to treat non-small cell lung cancer. Therapeutics of the invention can also be used to prevent progression from a pre-neoplastic or non-malignant state into a neoplastic or a malignant state.

Various delivery systems are known and can be used to administer a therapeutic agent of the invention, e.g., encapsulation in liposomes, microparticles, microcapsules, expression by recombinant cells, receptor-mediated endocytosis (see, e.g., Wu and Wu, (1987), *J. Biol. Chem.* 262:4429-4432), construction of a therapeutic nucleic acid as part of a retroviral or other vector, etc. Methods of delivery include but are not limited to intra-arterial, intra-muscular, intravenous, intranasal, and oral routes. In a specific embodiment, it may be desirable to administer the pharmaceutical compositions of the invention locally to the area in need of treatment; this may be achieved by, for example, and not by way of limitation, local infusion during surgery, by injection, or by means of a catheter.

The agents identified herein as effective for their intended purpose can be administered to subjects or individuals susceptible to or at risk of developing a disease correlated to the overexpression of these proto-oncogenes. When the agent is administered to a subject such as a mouse, a rat or a human patient, the agent can be added to a pharmaceutically acceptable carrier and systemically or topically administered to the subject. To determine patients that can be beneficially treated, a tumor sample is removed from the patient and the cells are assayed for the overexpression of the proto-oncogene. Therapeutic amounts can be empirically determined and will vary with the pathology being treated, the subject being treated and the efficacy and toxicity of the agent. When delivered to an animal, the method is useful to further confirm efficacy of the agent. As an example of an animal model, groups of nude mice (Balb/c NCR nu/nu female, Simonsen, Gilroy, Calif.) are each subcutaneously inoculated with about $10^5$ to about $10^9$ hyperproliferative, cancer or target cells as defined herein. When the tumor is established, the agent is administered, for example, by subcutaneous injection around the tumor. Tumor measurements to determine reduction of tumor size are made in two dimensions using venier calipers twice a week. Other animal models may also be employed as appropriate.

Administration in vivo can be effected in one dose, continuously or intermittently throughout the course of treatment. Methods of determining the most effective means and dosage of administration are well known to those of skill in the art and will vary with the composition used for therapy, the purpose of the therapy, the target cell being treated, and the subject being treated. Single or multiple administrations can be carried out with the dose level and pattern being selected by the treating physician. Suitable dosage formulations and methods of administering the agents can be found below.

The agents and compositions of the present invention can be used in the manufacture of medicaments and for the treatment of humans and other animals by administration in accordance with conventional procedures, such as an active ingredient in pharmaceutical compositions.

The pharmaceutical compositions can be administered orally, intranasally, parenterally or by inhalation therapy, and may take the form of tablets, lozenges, granules, capsules, pills, ampoules, suppositories or aerosol form. They may also take the form of suspensions, solutions and emulsions of the active ingredient in aqueous or nonaqueous diluents, syrups, granulates or powders. In addition to an agent of the present invention, the pharmaceutical compositions can also contain other pharmaceutically active compounds or a plurality of compounds of the invention.

More particularly, an agent of the present invention also referred to herein as the active ingredient, may be administered for therapy by any suitable route including oral, rectal, nasal, topical (including transdermal, aerosol, buccal and sublingual), vaginal, parental (including subcutaneous, intramuscular, intravenous and intradermal) and pulmonary. It will also be appreciated that the preferred route will vary with the condition and age of the recipient, and the disease being treated.

Ideally, the agent should be administered to achieve peak concentrations of the active compound at sites of disease. This may be achieved, for example, by the intravenous injection of the agent, optionally in saline, or orally administered, for example, as a tablet, capsule or syrup containing the active ingredient. Desirable blood levels of the agent may be maintained by a continuous infusion to provide a therapeutic amount of the active ingredient within disease tissue. The use of operative combinations is contemplated to provide therapeutic combinations requiring a lower total dosage of each component antiviral agent than may be required when each individual therapeutic compound or drug is used alone, thereby reducing adverse effects.

While it is possible for the agent to be administered alone, it is preferable to present it as a pharmaceutical formulation comprising at least one active ingredient, as defined above, together with one or more pharmaceutically acceptable carriers therefor and optionally other therapeutic agents. Each carrier must be "acceptable" in the sense of being compatible with the other ingredients of the formulation and not injurious to the patient.

Formulations include those suitable for oral, rectal, nasal, topical (including transdermal, buccal and sublingual), vaginal, parenteral (including subcutaneous, intramuscular, intravenous and intradermal) and pulmonary administration. The formulations may conveniently be presented in unit dosage form and may be prepared by any methods well known in the art of pharmacy. Such methods include the step of bringing into association the active ingredient with the carrier which constitutes one or more accessory ingredients. In general, the formulations are prepared by uniformly and intimately bringing into association the active ingredient with liquid carriers or finely divided solid carriers or both, and then if necessary shaping the product.

Formulations of the present invention suitable for oral administration may be presented as discrete units such as capsules, cachets or tablets, each containing a predetermined amount of the active ingredient; as a powder or granules; as a solution or suspension in an aqueous or non-aqueous liquid; or as an oil-in-water liquid emulsion or a water-in-oil liquid emulsion. The active ingredient may also be presented a bolus, electuary or paste.

A tablet may be made by compression or molding, optionally with one or more accessory ingredients. Compressed tablets may be prepared by compressing in a suitable machine the active ingredient in a free-flowing form such as a powder or granules, optionally mixed with a binder (e.g., povidone, gelatin, hydroxypropylmethyl cellulose), lubricant, inert diluent, preservative, disintegrant (e.g., sodium starch glycolate, cross-linked povidone, cross-linked sodium carboxymethyl cellulose) surface-active or dispersing agent. Molded tablets may be made by molding in a suitable machine a mixture of the powdered compound moistened with an inert liquid diluent. The tablets may optionally be coated or scored and may be formulated so as to provide slow or controlled release of the active ingredient therein using, for example, hydroxypropylmethyl cellulose in varying proportions to provide the desired release profile. Tablets may optionally be provided with an enteric coating, to provide release in parts of the gut other than the stomach.

Formulations suitable for topical administration in the mouth include lozenges comprising the active ingredient in a flavored basis, usually sucrose and acacia or tragacanth; pastilles comprising the active ingredient in an inert basis such as gelatin and glycerin, or sucrose and acacia; and mouthwashes comprising the active ingredient in a suitable liquid carrier.

Pharmaceutical compositions for topical administration according to the present invention may be formulated as an ointment, cream, suspension, lotion, powder, solution, past, gel, spray, aerosol or oil. Alternatively, a formulation may comprise a patch or a dressing such as a bandage or adhesive plaster impregnated with active ingredients and optionally one or more excipients or diluents.

If desired, the aqueous phase of the cream base may include, for example, at least about 30% w/w of a polyhydric alcohol, i.e., an alcohol having two or more hydroxyl groups such as propylene glycol, butane-1,3-diol, mannitol, sorbitol, glycerol and polyethylene glycol and mixtures thereof. The topical formulations may desirably include a compound which enhances absorption or penetration of the agent through the skin or other affected areas. Examples of such dermal penetration enhancers include dimethylsulfoxide and related analogues.

The oily phase of the emulsions of this invention may be constituted from known ingredients in an known manner. While this phase may comprise merely an emulsifier (otherwise known as an emulgent), it desirably comprises a mixture of at lease one emulsifier with a fat or an oil or with both a fat and an oil. Preferably, a hydrophilic emulsifier is included together with a lipophilic emulsifier which acts as a stabilizer. It is also preferred to include both an oil and a fat. Together, the emulsifier(s) with or without stabilizer(s) make up the so-called emulsifying wax, and the wax together with the oil and/or fat make up the so-called emulsifying ointment base which forms the oily dispersed phase of the cream formulations.

Emulgents and emulsion stabilizers suitable for use in the formulation of the present invention include Tween 60, Span 80, cetostearyl alcohol, myristyl alcohol, glyceryl monostearate and sodium lauryl sulphate.

The choice of suitable oils or fats for the formulation is based on achieving the desired cosmetic properties, since the solubility of the active compound in most oils likely to be used in pharmaceutical emulsion formulations is very low. Thus the cream should preferably be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters known as Crodamol CAP may be used, the last three being preferred esters. These may be used alone or in combination depending on the properties required. Alternatively, high melting point lipids such as white soft paraffin and/or liquid paraffin or other mineral oils can be used.

Formulations suitable for topical administration to the eye also include eye drops wherein the active ingredient is dissolved or suspended in a suitable carrier, especially an aqueous solvent for the agent.

Formulations for rectal administration may be presented as a suppository with a suitable base comprising, for example, cocoa butter or a salicylate.

Formulations suitable for vaginal administration may be presented as pessaries, tampons, creams, gels, pastes, foams or spray formulations containing in addition to the agent, such carriers as are known in the art to be appropriate.

Formulations suitable for nasal administration, wherein the carrier is a solid, include a coarse powder having a particle size, for example, in the range of about 20 to about 500 microns which is administered in the manner in which snuff is taken, i.e., by rapid inhalation through the nasal passage from a container of the powder held close up to the nose. Suitable formulations wherein the carrier is a liquid for administration as, for example, nasal spray, nasal drops, or by aerosol administration by nebulizer, include aqueous or oily solutions of the agent.

Formulations suitable for parenteral administration include aqueous and non-aqueous isotonic sterile injection solutions which may contain anti-oxidants, buffers, bacteriostats and solutes which render the formulation isotonic with the blood of the intended recipient; and aqueous and non-aqueous sterile suspensions which may include suspending agents and thickening agents, and liposomes or other microparticulate systems which are designed to target the compound to blood components or one or more organs. The formulations may be presented in unit-dose or multi-dose sealed containers, for example, ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules and tablets of the kind previously described.

Preferred unit dosage formulations are those containing a daily dose or unit, daily subdose, as herein above-recited, or an appropriate fraction thereof, of a agent.

It should be understood that in addition to the ingredients particularly mentioned above, the formulations of this invention may include other agents conventional in the art having regard to the type of formulation in question, for example, those suitable for oral administration may include such further agents as sweeteners, thickeners and flavoring agents. It also is intended that the agents, compositions and methods of this invention be combined with other suitable compositions and therapies.

In another aspect, the proto-oncogenes provided herein can be used to generate transgenic animal models. In recent years, geneticists have succeeded in creating transgenic animals, for example mice, by manipulating the genes of developing embryos and introducing foreign genes into these embryos. Once these genes have integrated into the genome of the recipient embryo, the resulting embryos or adult animals can be analyzed to determine the function of the gene. The mutant animals are produced to understand the function of known genes in vivo and to create animal models of human diseases. (see, e.g., Chisaka et al. (1992) 355:516-520; Joyner et al. (1992) in POSTIMPLANTATION DEVELOPMENT IN THE MOUSE (Chadwick and Marsh, eds., John Wiley & Sons, United Kingdom) pp: 277-297; Dorin et al. (1992) Nature 359:211-215).

U.S. Pat. Nos. 5,464,764 and 5,487,992 describe one type of transgenic animal in which the gene of interest is deleted or mutated sufficiently to disrupt its function. (See, also U.S. Pat. Nos. 5,631,153 and 5,627,059). These "knock-out" animals, made by taking advantage of the phenomena of homologous recombination, can be used to study the function of a particular gene sequence in vivo. The polynucleotide sequences described herein are useful in preparing animal models of lung cancer.

The following examples are intended to illustrate, but not limit this invention.

EXAMPLES

Methods

SAGE Analysis of cDNAs Derived from Tumor or Normal Lungs

Primary squamous cell lung cancers containing over 95% neoplastic components from two unrelated patients were selected for SAGE analysis. Patient A was 58-year old and diagnosed with moderately differentiated cancer at the lower right lobe of the lung at the time of surgery. Patient B was 68-year old and diagnosed with poorly differentiated cancer of the lower right lobe. Normal small airway epithelial cells obtained from two age and gender-matched independent individuals were used as the negative controls. All cancer cell lines were obtained from the American Type Culture Collection and propagated according to the instructions provided.

A systematic analysis of transcripts present in non-small cell lung cancer (NSCLC) was performed by Serial Analysis of Gene Expression ("SAGE") (U.S. Pat. No. 5,695,937). SAGE analysis involves identifying nucleotide sequences expressed in the antigen-expressing cells. Briefly, SAGE analysis begins with providing complementary deoxyribonucleic acid (cDNA) from (1) the neoplastic population and (2) normal cells. Both cDNAs can be linked to primer sites. Sequence tags are then created, for example, using the appropriate primers to amplify the DNA. By measuring the differences in these tags between the two cell types, sequences which are aberrantly expressed in the neoplastic cell population can be identified.

The SAGE libraries were constructed essentially as described in Velculescu et al. (1995) Science 270:484-487. PolyA RNAs isolated from lung tumors of patients A and B, and from normal small airway epithelial cells were converted to double-stranded cDNA. The cDNA was then cleaved with an anchoring enzyme NlaIII and divided into two pools. Linkers containing recognition sites for the tagging enzyme BsmFI was ligated to each pool: After BsmF1 restriction, SAGE tag overhangs were filled-in with Klenow, and tags from the two pools were combined and ligated to each other. The ligation product was diluted and then amplified by PCR. The resulting PCR product was then analyzed by polyacrylamide gel electrophoresis (PAGE), and the PCR product containing two tags ligated tail to tail (ditag) was excised and then cleaved with NlaIII. After NlaIII restriction, the ditags was excised and self-ligated. The concatenated products were separated by PAGE and those containing ~500 to 2000 nucleotide base pairs were excised and cloned for subsequent sequence analysis.

The sequence and the occurrence of each of the transcript tags was determined using SAGE software, described, for example in Venter et al. (1996) Nature 381:364-366. To identify transcript tags present in each library, the sequences of all SAGE tags were stores as "tag" file in Microsoft Access. The GenBank dbEST and nucleotide databases were also analyzed by the SAGE software to identify the corresponding SAGE tags and then stored as a "Genename." The GenBank entry for each SAGE tag was obtained by linking the tags from the Tag and Genename files using Microsoft Access. the relative occurrence of each tag was determined by comparing the number of tags observed in the tumor libraries with that observed in the normal control libraries. The relative abundance for the tags was calculated by dividing the total number of tags observed with the total number of tags identified.

Northern Blot Analysis

To establish the clinical significance of the differential expression of the SAGE transcripts in lung tumorigenesis, Northern blot analysis was performed using total RNA from normal tissues and a panel of NSCLC cell lines using oligonucleotide probes complementary to the transcripts of PGP9.5, b-myb or 8-oxo-dGTPase. Procedures for carrying out Northern blot analysis are detailed in CURRENT PROTOCOLS IN MOLECULAR BIOLOGY, supra. In primary lung tumors, a low 8-oxo-dGTPase mRNA level was detected in 3/8 cases examined. However, PGP9.5 mRNA was overexpressed in 10/18 cases and b-myb was overexpressed in 15/18 cases. Whereas transcripts of these genes were not detected in normal lung cell sample, they were invariably detected in more than 90% of the examined lung tumor cell lines (see Table 2).

Comparative Northern blot analyses of the normal cell lines and NSCLC cell lines (see FIGS. 2 and 3) confirmed an increase in PGP9.5, 8-oxo-dGTPase or b-myb mRNA levels in NSCLC cells, thus establishing an involvement of these two genes in lung tumorigenesis, and particularly in non-small cell lung cancer.

Western Blot Analysis

Cell lysates from $5 \times 10^4$ cells of each cell line described herein were electrophoresed on a 4-20% SDS gradient gel and transferred to a PVDF membrane (MSI). After blocking non-specific site by incubating in PBS+5% non-fat dry milk (NFDM), the membrane was incubated with anti-PGP 9.5 antibody (Biogenesis, UK) at 1:400 dilution. ECL kit (Amersham) was used to visualize the antibody binding to PGP9.5 protein (see FIG. 3B bottom panel).

Results

Four independent SAGE libraries were constructed from messenger RNAs using two squamous cell lung cancers and two normal lung small airway epithelial cell cultures as described in Madden et al. (1997) Oncogene 15:1079-1085.

A total of 2,000-4,000 clones were sequenced to identify more than 50,000 transcripts tags from each library (Table 1). The sequences of over 50,000 tags that represent about 15,000 unique transcripts in each library were analyzed in order to generate a comprehensive profile of gene expression patterns in lung cancer. In total, 226,876 tags were sequenced, jointly representing 43,254 unique transcripts. GenBank analysis suggested that about 40% of the SAGE tags had at least one match in the database. As summarized in Table 1, an examination of the SAGE tags identified from each sample indicated that the occurrence of tags within each tissue type was highly consistent because only 15 and 17 tags were differentially expressed by more than 10 fold when the two normal control libraries were compared with each other. Similarly, 36 and 39 tags, respectively, were expressed differentially by more than 10-fold between the two tumors. Therefore, the SAGE tags obtained from the two normal controls and the two tumors were combined to determined the total number of occurrence for each tag.

A comparison of the number of tags present in the tumor and normal libraries indicated that a majority of the transcripts were expressed at similar levels (FIG. 1). However, 142 transcripts were overexpressed 10 folds or more in the tumor and about 175 as many were overexpressed in the normal control. Table 1 summarizes the comparative SAGE analyses of cDNA clones derived from the lung cancers of two individuals and the lungs of two normal individuals.

TABLE 1

Summary of SAGE analysis.

|  | Tumor A | Tumor B | Normal Lung 1 | Normal Lung 2 | Overall |
|---|---|---|---|---|---|
| Total clones | 2,259 | 2,186 | 3,759 | 4,046 | 12,250 |
| Total tags | 56,817 | 51,901 | 58,273 | 59,885 | 226,876 |
| Unique tags | 17,535 | 16,443 | 15,070 | 15,667 | 43,254 |
| GenBank match[a] | 8,867 | 8,445 | 7,596 | 7,801 | 18,553 |
| Tags > 10X[b] | 36 | 39 | 17 | 25 | 142/175 |

[a] The number of tags that matched an entry in GenBank
[b] Number of tags that were differentially expressed at the indicated folds when compared to each other. The overall values (tumor/normal) were obtained by comparing the tags identified in the two tumors (A and B) with those in the two normal samples (1 and 2).

All tags were searched against GenBank to identify the corresponding gene transcripts or EST clones. The highest level of relative gene expression in the normal control was about 150 fold (data not shown), whereas the highest level of expression in the tumor was 57 fold compared to the normal control.

In order to identify genes that were consistently overexpressed in most lung cancers but not present in the normal lung, each candidate gene was screened by Northern blot analyses using total RNA from normal lung, liver, small intestine, and 9 lung tumor cell lines. (See FIG. 2).

Figure 2:
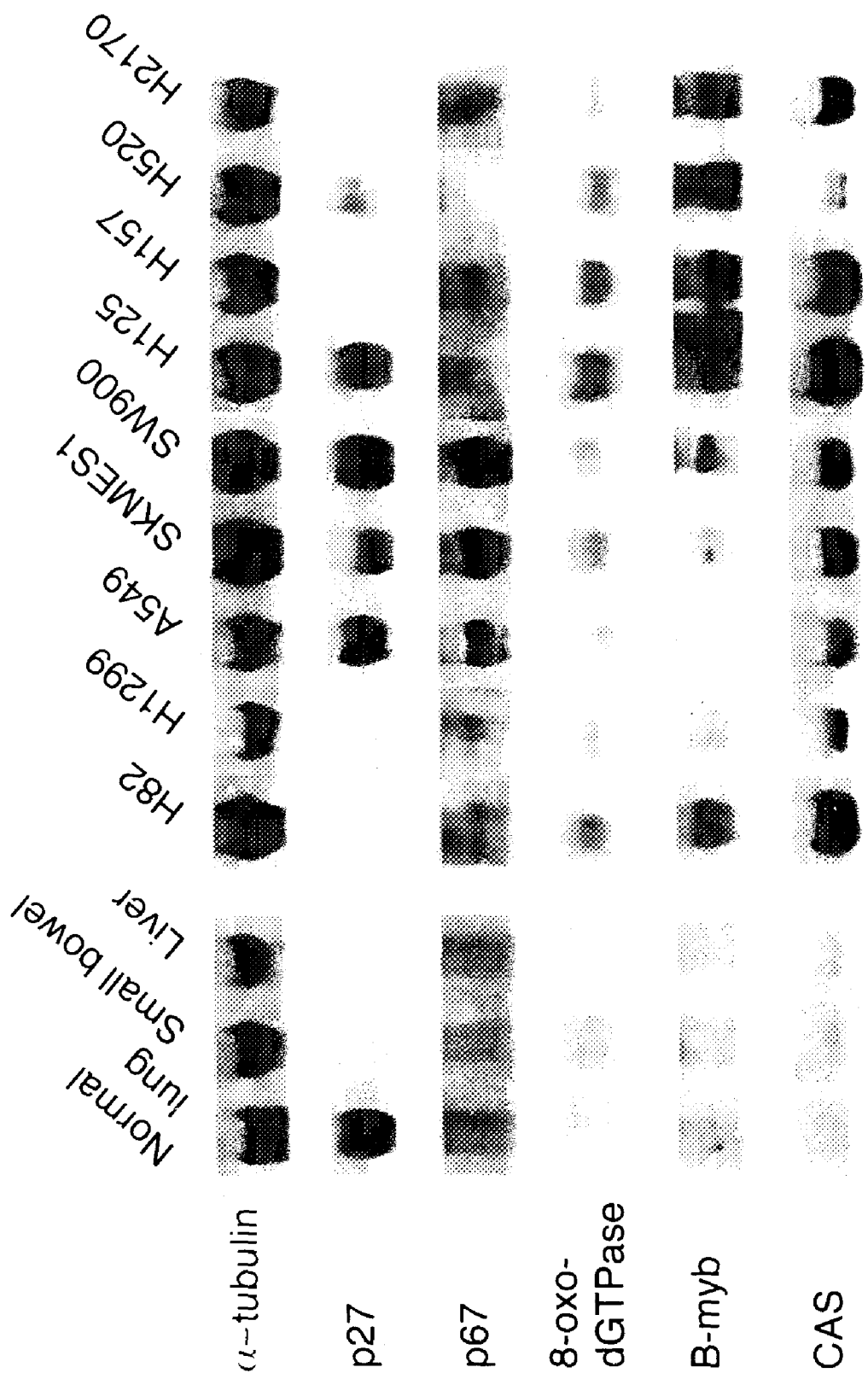
FIG. 2 depicts Northern blot analysis of genes identified by SAGE. Total RNAs were isolated from normal lung, small bowel, liver, and a panel of 9 lung tumor cell lines as indicated. All cell lines were obtained from ATCC and previously described in Gazdar et al. (1996) J. Cell Biochem. Suppl. 24:1-11; and Phelps et al. (1996) J. Cell Biochem Suppl. 24:32-91.
Figure 3A:
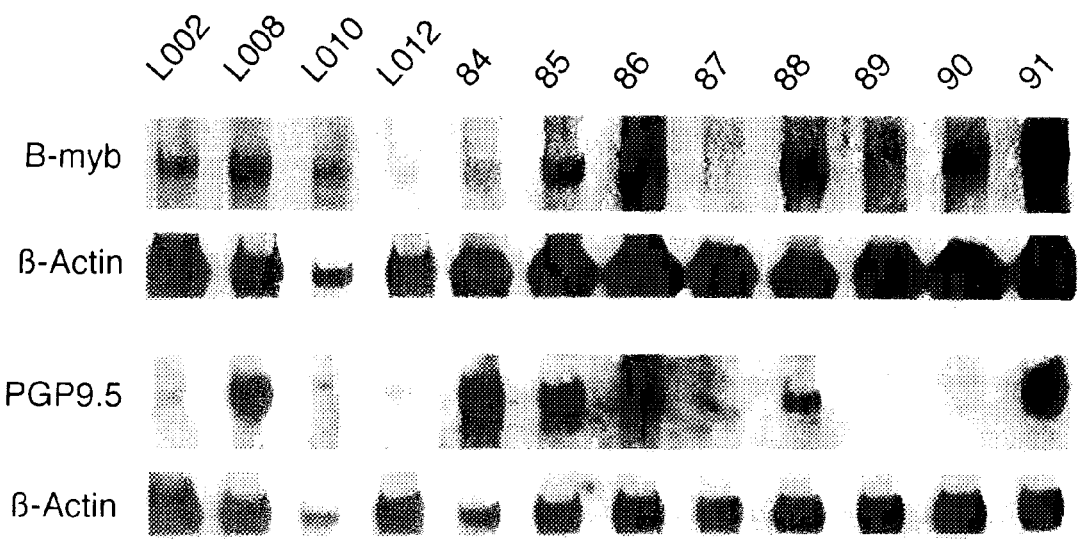
FIG. 3A depicts the detection of the human b-myb and PGP9.5 transcripts in primary lung cancers. Upper panel: cases L002, L008, L010, L012, 84, 85, 86, 88, 90, 91 have b-myb transcripts in their lung tumors. Lower panel: cases L002, L008, L012, 84, 85, 86, 88, 91 have PGP9.5 transcripts in their lung tumors.
Figure 3B:
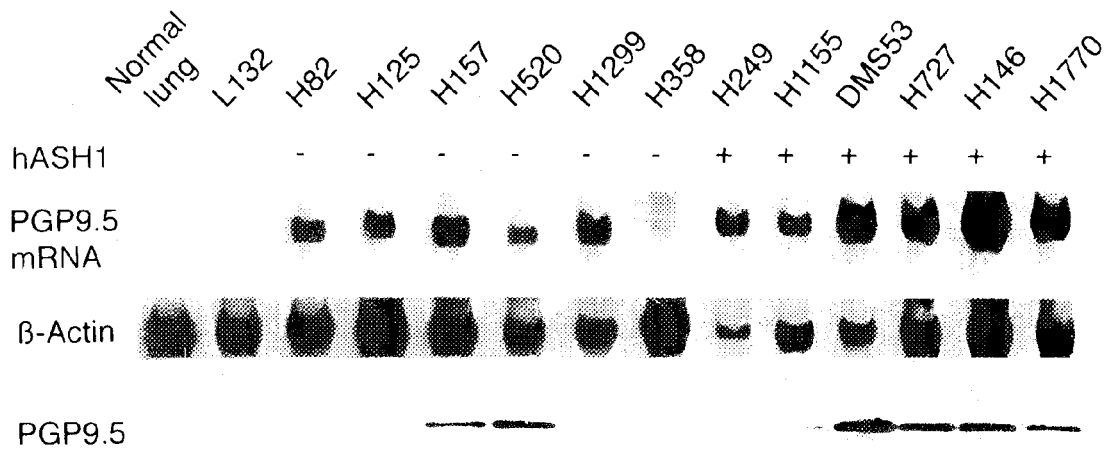
FIG. 3B depicts expression pattern of the human PGP9.5 transcript in lung cancer cell lines of different ASH1 status. PGP9.5 transcript was not detectable in either normal lung or an embryonic lung cell line (L132) but was expressed in lung tumor cell lines with (H82, H125, H157, H520, H1299, H358) and without (H249, H1155, DMS53, H727, H146, H1770) neuroendocrine features. H358 has lower expression compared to other cell lines. The bottom panel depicts a Western blot using anti-PGP9.5 antibody for detecting PGP9.5 protein expressed in lung tumor cell lines. PGP9.5 was expressed in all cell lines except H358.

The transcripts to 15 significantly overexpressed tags with authentic EST or GenBank matches have been examined. Among the tested genes, 10 were excluded from further analysis because they were either commonly expressed (6 genes) or virtually absent (4 genes) in most tissues and cell lines. (See, Table 2). Interferon-α-inducible gene was detected in the normal lung and therefore was not further analyzed. The transcripts for four genes, each encoding 8-oxo-dGTPase (human MutT), b-myb, p67 or PGP9.5, were not detectable in the normal lung samples but were easily detectable in most of the lung cancer cell lines tested (FIGS. 2 and 3B). The abundance of these four genes ranged form 0.012% to 0.018% of the total tags identified in the tumor or about 36-54 transcripts/cell, assuming that there are approximately 300,000 transcripts in a cell.

TABLE 2

Northern blot analysis of genes overexpressed in NSCLC

| SEQ ID NO | Tag sequence | T/N | Gene name | Accession no. | Lung | Small Bowel | Liver | Lung tumor cell lines (n = 9) |
|---|---|---|---|---|---|---|---|---|
| 5 | TGTACCTGTA | 133/3 | α-tubulin | K00558 | + | + | + | 9* |
| 6 | GCTTGAATAA | 53/1 | EST 1 | AA101952 | + | + | + | 9 |
| 7 | ATGCAGCCAT | 48/5 | ornithine decarboxylase | M81470 | nd | + | + | 9 |
| 8 | CTCCTGGGCG | 37/0 | NB-1 | M58026 | − | − | − | 0 |
| 9 | CCAGGGGAGA | 37/1 | interferon-α-inducible gene | X67325 | + | − | − | 6 |
| 10 | CTGAGACGAA | 34/0 | BTF3b | X53281 | + | + | + | 8 |
| 11 | GATAGCACAG | 32/0 | IGF binding protein | L27560 | nd | − | − | 1 |
| 12 | TATCTGTCTA | 30/2 | EST 2 | D29035 | + | + | + | 9 |
| 13 | TAATACTTTT | 20/0 | initiation factor 2-associated protein | U13261 | − | − | − | 6 |
| 14 | CAATAAAATT | 18/0 | EST 3 | W72411 | − | − | − | 1 |
| 15 | AAGGCTGGAA | 16/0 | EST 4 | AA663132 | − | − | − | 0 |

TABLE 2-continued

Northern blot analysis of genes overexpressed in NSCLC

| SEQ ID NO | Tag sequence | T/N | Gene name | Accession no. | Lung | Small Bowel | Liver | Lung tumor cell lines (n = 9) |
|---|---|---|---|---|---|---|---|---|
| 3 | TGGCCCGACG | 15/0 | 8-oxo-dGTPase | D16581 | − | + | − | 9 |
| 16 | TTCTGTGCTG | 15/0 | selenophosphate synthetase 2 | U43286 | + | + | + | 9 |
| 2 | CAGTCTAAAA | 15/0 | PGP9.5 | X04741 | − | − | − | 8 |
| 1 | TGCTGCCCTG | 13/0 | B-myb | X13293 | − | + | − | 9 |
| 17 | ATCCTGTAGG | 13/1 | cellular apotosis susceptibility gene | U33286 | + | + | + | 9 |
| 4 | TAATACTTTT | 20/0 | p67 | U13261 | − | nd | nd | 6 |

T/N indicates fold of overexpression in the tumor.
"+": transcript detected by Northern; "−": transcript not detectable by Northern; nd: not determined.
*Indicates the number of cell lines with detectable message among the 9 cell lines tested.

In Table 2, the values on the left sum of SAGE tags identified in tumor (T) or normal libraries (N). The results of the Northern analysis are shown at the right of the table. All lung tumor cell lines (H82, H1299, A549, SKEM, SW900, H125, H157, H520, H2170, and L132) were obtained from ATCC and propagated according to the instructions. Except for L132, all other cell lines were derived from lung cancers.

To determine the biological relevance of overrepresentation of these transcripts, the presence of these transcripts in primary tumors was examined. It was found that b-myb transcripts were overexpressed in 15/18 primary tumors (see FIG. 3A upper panel that depicts results from selected primary tumor samples) and the PGP9.5 mRNAs were overexpressed in 10/18 primary tumors. 8-oxo-dGTPase was detected in 38 samples (see FIG. 3A lower panel and also Table 3 that summarizes the expression pattern of the human PGP9.5 gene transcript in all examined primary lung cancers). Interestingly, all four lung cancer cases with lymph node metastases expressed the PGP9.5 message, showing a possible correlation of PGP9.5 overexpression and clinical manifestation of the disease.

TABLE 3

Expression of PGP9.5 gene in primary lung cancer

| Primary lung tumor | Northern blot analysis | Histology | Lymphnode metastasis |
|---|---|---|---|
| L002 | + | adeno | − |
| L004 | − | adeno | − |
| L006 | − | adeno | − |
| L008 | + | adeno | + |
| L010 | − | squamous | − |
| L012 | + | adeno + small cell | − |
| L014 | − | bronchioaleolar | − |
| L016 | − | adeno | − |
| 1T | + | squamous | + |
| 3T | + | squamous | + |
| 84 | + | squamous | − |
| 85 | + | squamous | − |
| 86 | + | squamous | − |
| 87 | − | squamous | − |
| 88 | + | squamous | + |
| 89 | − | squamous | − |
| 90 | − | squamous | − |
| 91 | + | squamous | − |

Since lung cancers often have features of neuronal differentiation (Mackay, et al. (1990) Tumors of the Lung in MAJOR PROBLEMS IN PATHOLOGY, Volume 24, W.B. Saunders Co. Philadelphia), and PGP 9.5 gene was originally identified as a neuro-specific ubiquitinhydrolase (Wilkinson, et al. (1989) Science 246:670-673), it was next determined whether PGP9.5 expression was associated with this phenotype. A panel of established lung cancer cell lines having defined neuroendocrine features based on hASH1 gene status (see Borges, et al. (1997) Nature 386:852-855) were used. Although expression of hASH1 is essential for neurodifferentiation of the lung and is one of the most reliable neuroendocrine markers (Ermisch, et al. (1995) Clin. Neuropath. 3:130-136), PGP9.5 protein was abundantly expressed in nearly all lung cancer cell lines independent of hASH1 status (FIG. 3B).

It is also possible that PGP9.5 expression was associated with the high rate of proliferation common to all cancers. To address this issue, a panel of 12 head and neck cancer and bladder cancer cell lines were tested to determine the tissue specificity of PGP9.5 overexpression. Head and neck cancers are invariably derived from squamous cell origin and usually have histopathological and genetic characteristics similar to those of squamous cell lung cancer. However, only 3 of the 6 head and neck tumor cell lines had PGP9.5 message and none of the 12 cancers expressed the encoded protein (see Table 4). These observations show that the overexpression of PGP9.5 is primarily restricted to lung cancers and that the presence of PGP9.5 protein is independent of neuronal differentiation but may contribute to lung tumor development by deubiquitination of target proteins.

TABLE 4

PGP9.5 expression and the character of other tumors.

| Cell line | Northern blot analysis | Histology |
|---|---|---|
| FADU | − | head and neck cancer |
| 022 | + | head and neck cancer |
| 06 | + | head and neck cancer |
| 11 | − | head and neck cancer |
| 12 | + | head and neck cancer |
| 29 | − | head and neck cancer |

TABLE 4-continued

PGP9.5 expression and the character of other tumors.

| Cell line | Northern blot analysis | Histology |
|---|---|---|
| J82 | − | bladder cancer |
| SCaBER | − | bladder cancer |
| T24 | − | bladder cancer |
| S637 | − | bladder cancer |
| HT1376 | − | bladder cancer |
| HT1197 | − | bladder cancer |

Table 5 shows expression of PGP9.5 and B-myb in human cancers as determined by Northern blot analysis. Both PGP9.5 and B-myb were expressed at much lower frequencies in primary cancers derived from colon, bladder and kidney.

TABLE 5

Expression of PGP9.5 and B-myb in human cancers

| Tumor Type | PGP9.5 (%) | B-myb (%) |
|---|---|---|
| Lung cell lines | 22/23 (96) | 23/23 (100) |
| Primary Cancer | | |
| Lung | 10/18 (56) | 15/18 (83) |
| Colon | 0/5 (0) | 0/5 (0) |
| Bladder | 0/4 (0) | 2/4 (50) |
| Kidney | 2/7 (29) | 1/7 (14) |

It is to be understood that while the invention has been described in conjunction with the above embodiments, that the foregoing description and the following examples are intended to illustrate and not limit the scope of the invention. Other aspects, advantages and modifications within the scope of the invention will be apparent to those skilled in the art to which the invention pertains.

The invention claimed is:

1. A method for detecting and diagnosing lung cancer in a human patient, said method comprising:
   (a) detecting the presence of an overexpressed b-mvb proto-oncogene in a lung cell sample taken from the patient; and
   (b) determining that there is an indication of the presence of lung cancer in the patient when the proto-oncogene is overexpressed.

2. A method for identifying a human patient having lung cancer, said method comprising:
   (a) determining the expression level of the b-myb proto-oncogene in a lung cell sample isolated from the patient; and
   (b) identifying the patient as likely to have lung cancer when the expression level of the proto-oncogene in the sample is above the level of expression of the proto-oncogene in normal lung cells.

3. The method of claim 1 or 2, further comprising:
   (a) determining the expression level of the PGP9.5 proto-oncogene in a lung cell sample isolated from the patient; and
   (b) determining that there is a further indication of the presence of lung cancer in the patient when the PGP9.5 proto-oncogene is overexpressed.

4. The method of claim 2, wherein determining the expression level of the b-myb proto-oncogene comprises measuring the quantity of mRNA transcribed from the b-myb proto-oncogene in the sample.

5. The method of claim 2, wherein determining the expression level of the b-myb proto-oncogene comprises measuring the quantity of cDNA produced from the reverse transcription of the b-myb mRNA in the sample.

6. The method of claim 2, wherein determining the expression level of the b-myb proto-oncogene comprises measuring the quantity of the polypeptide or protein encoded by the b-myb proto-oncogene in the sample.

7. The method of claim 1 or 2, wherein the lung cancer is non-small cell lung cancer.

8. The method of claim 2, wherein determining the expression level of the b-myb proto-oncogene comprises probing the lung cell sample with a probe or primer comprising the sequence TGCTGCCCTG (SEQ. ID No. 1) or its complement.

9. The method of claim 1, wherein detecting the presence of an overexpressed b-mvb proto-oncogene in a lung cell sample taken from the patient comprises measuring the quantity of mRNA transcribed from the b-myb proto-oncogene in the sample.

10. The method of claim 1, wherein detecting the presence of an overexpressed b-mvb proto-oncogene in a lung cell sample taken from the patient comprises measuring the quantity of mRNA transcribed from the b-myb proto-oncogene in the sample.

11. The method of claim 1, wherein detecting the presence of an overexpressed b-mvb proto-oncogene in a lung cell sample taken from the patient comprises measuring the quantity of cDNA produced from the reverse transcription of the b-myb mRNA in the sample.

12. The method of claim 1, wherein detecting the presence of an overexpressed b-mvb proto-oncogene in a lung cell sample taken from the patient comprises measuring the quantity of the polypeptide or protein encoded by the b-myb proto-oncogene in the sample.

13. The method of claim 1, wherein detecting the presence of an overexpressed b-mvb proto-oncogene in a lung cell sample taken from the patient comprises probing the lung cell sample with a probe or primer comprising the sequence TGCTGCCCTG (SEQ. ID No. 1) or its complement.

* * * * *